United States Patent [19]

Samuelson et al.

[11] Patent Number: 5,361,776
[45] Date of Patent: Nov. 8, 1994

[54] TIME DOMAIN REFLECTOMETER IMPEDANCE SENSOR METHOD OF USE AND IMPLANTABLE CARDIAC STIMULATOR USING SAME

[75] Inventors: Kent E. Samuelson, Aurora; Robert A. Morris, Palmer Lake; James A. Nolan, Conifer; Bruce M. Steinhaus, Parker, all of Colo.

[73] Assignee: Telectronics Pacing Systems, Inc., Englewood, Colo.

[21] Appl. No.: 104,382

[22] Filed: Aug. 6, 1993

[51] Int. Cl.⁵ ............................................. A61B 5/05
[52] U.S. Cl. .................................... 128/734; 607/9
[58] Field of Search ............... 607/4, 5, 9, 19, 29, 607/62; 128/693, 723, 734

[56] References Cited

U.S. PATENT DOCUMENTS

| | | |
|---|---|---|
| 4,692,719 | 9/1987 | Whigham .......................... 332/11 D |
| 4,702,253 | 10/1987 | Nappholz et al. ............ 128/419 PG |
| 4,901,725 | 2/1990 | Nappholz et al. ............ 128/419 PG |
| 4,970,466 | 11/1990 | Bolles et al. ........................ 324/533 |
| 5,134,377 | 7/1992 | Reddy, III et al. ................ 324/533 |
| 5,197,467 | 3/1993 | Steinhaus et al. ............ 128/419 PG |
| 5,231,987 | 8/1993 | Robson . | |
| 5,233,986 | 8/1993 | Robson . | |
| 5,251,622 | 10/1993 | Robson . | |

*Primary Examiner*—William E. Kamm
*Attorney, Agent, or Firm*—Gottlieb, Rackman, Reisman

[57] ABSTRACT

A time domain reflectometry (TDR) impedance sensor is provided for measuring body impedance along a lead or catheter implanted in a patient's cardiovascular system. The TDR sensor applies an electrical stimulus to the lead and measures reflections echoed from impedance variations along and distal to the lead, which are superimposed on the applied stimulus. The measured signals may be analyzed with respect to time-of-flight and distance along the lead to detect a plurality of physiologically meaningful signals.

34 Claims, 11 Drawing Sheets

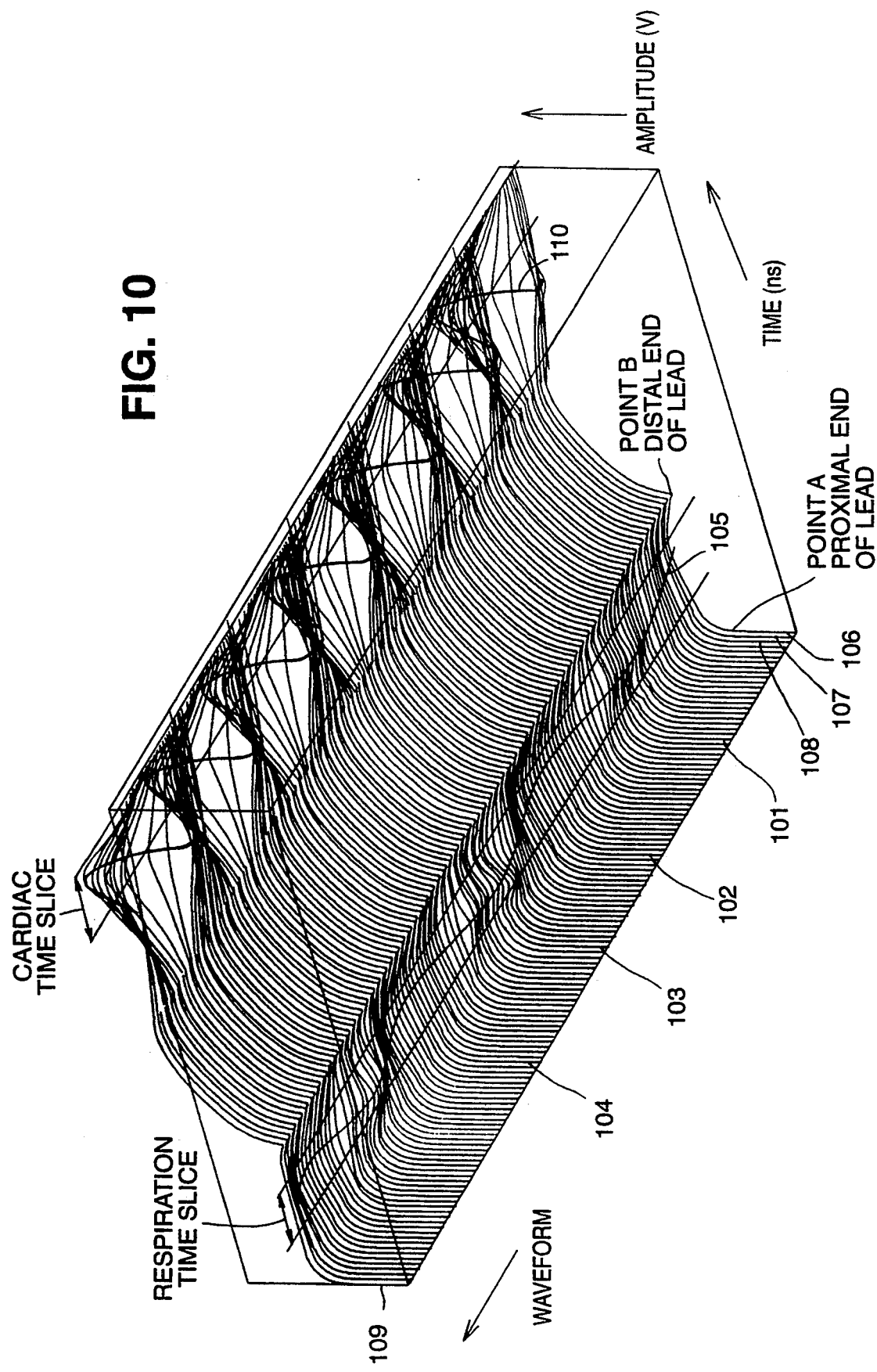

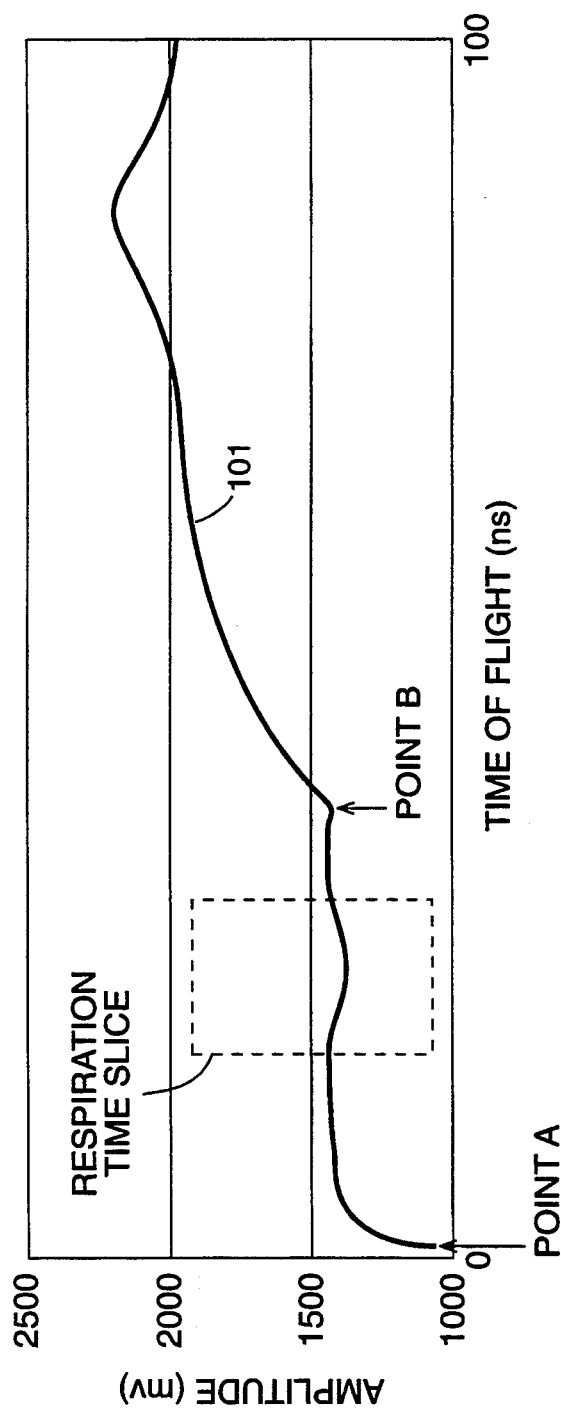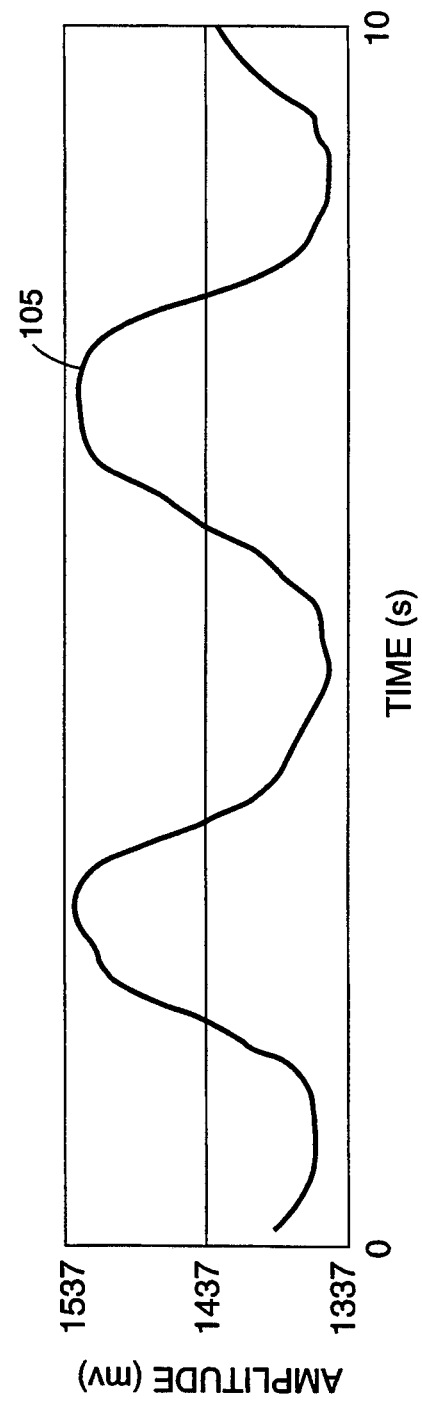

TIME DOMAIN REFLECTOMETER IMPEDANCE SENSOR METHOD OF USE AND IMPLANTABLE CARDIAC STIMULATOR USING SAME

TECHNICAL FIELD

This invention relates to body impedance sensors, and more particularly to body impedance sensors that sense body impedance using time domain reflectometry analysis.

DESCRIPTION OF THE PRIOR ART

Impedance sensors have been used for various purposes in implantable medical devices. In U.S. Pat. No. 4,702,253, entitled "Metabolic-Demand Pacemaker and Method of Using the Same to Determine Minute Volume", issued Oct. 27, 1987, T. A. Nappholz et al. disclose a rate-responsive pacemaker which measures blood impedance to derive a respiratory minute volume pacing rate control parameter. This pacemaker (hereinafter called the "'253 pacemaker") measures impedance by providing a three-electrode lead using one electrode to sense heart signals and pace the patient's heart in the conventional manner and employing the remaining two electrodes to perform the impedance measurement. A three-electrode lead is not a standard lead in the art of cardiac pacing. The two electrodes for measuring impedance are located in a blood vessel in the vicinity of the patient's pleural cavity. The '253 pacemaker periodically applies current pulses between one of the electrodes and the pacemaker case, and measures the voltage resulting from the applied current between the other electrode and the pacemaker case. The measured voltage is a function of the blood impedance in the vessel which, in turn, is dependent upon the pleural pressure. The '253 pacemaker determines the minute volume by monitoring the modulation in the impedance measurement. A problem with the '253 pacemaker is that it requires a nonstandard lead, a lead having at least three electrodes. Unipolar (single electrode)-and bipolar (dual electrode) leads are standard in the art of cardiac pacing. There are many patients with implanted unipolar and bipolar leads, and if a three-electrode lead is required for a new pacemaker, then a prior art non-rate-responsive pacemaker cannot be replaced by a rate-responsive pacemaker simply by exchanging pacemakers and using the same lead.

U.S. Pat. No. 4,901,725, entitled "Minute Volume Rate-Responsive Pacemaker, issued Feb. 20, 1990, in the names of T. A. Nappholz et al., discloses an improved minute volume-controlled rate-responsive pacemaker (hereinafter called the "'725 pacemaker") adapted to be used with a conventional bipolar lead. Such a bipolar lead has two electrodes for sensing and pacing the heart. In the '725 pacemaker a ring electrode, in addition to being used for sensing and pacing, is used to apply a current which flows to the pacemaker case. A tip electrode, in addition to being used for sensing and pacing, is used to measure the blood impedance between the tip and the case in response to the current pulse applied through the ring electrode. The '725 pacemaker utilizes the measured blood impedance to derive an appropriate pacing rate.

Although the '725 pacemaker uses bipolar leads which are standard in cardiac pacing, it has a limitation in that this pacemaker cannot be used in the many patients who have had previously implanted unipolar leads. Unipolar leads, which have a single tip electrode, are also standard in the art of cardiac pacing. If a bipolar lead is required when a patient has a new pacemaker implanted, then a non-rate-responsive pacemaker that is connected to a unipolar lead cannot be replaced by a '725 rate-responsive pacemaker simply by exchanging pacemakers and using the same lead.

Previous attempts have been made to perform minute volume rate-responsive pacing in a pacemaker using unipolar leads. These attempts failed, primarily because the blood impedance signal measured from unipolar leads was too weak in comparison to system noise and other unwanted signals present. A primary source of noise, which obscures impedance signals from a unipolar lead, is the electrolytic effect at the interface between the metal electrode and body fluid electrolytes. The pacemaker generates a net charge at the electrode for pacing the heart and, in the rate-responsive pacemaker of the '253 and '725 pacemakers as well as in the pacemaker of the present invention, for measuring blood impedance. This net charge within the metal is positive at the anode and negative at the cathode of the tip and ring electrodes. An opposing charge distribution develops in the electrolyte due to the charge distribution within the electrodes. This opposing charge is held from the metal surface by the forces of reduction and oxidation chemical reactions, which occur whenever a metal is placed in an electrolytic solution. The charge separation distance is approximately the thickness of a molecular layer of water.

The charged layers at the electrode-electrolyte interface constitute a charged capacitance in which the charges are held together by electrostatic forces. The magnitude of the capacitance depends inversely on the separation of the charged layers. This separation is very small, on the order of the dimension of molecular water. Therefore, the capacitance is remarkably large, in the range of 1 to 20 $\mu F/cm^2$. The presence of a large capacitance at the tip electrode causes a large DC impedance. The injection of current on the electrode causes a disturbance at the electrode-electrolyte interface which takes the form of a large, slowly decaying polarization potential at the tip electrode. Thus, when a pacemaker generates a conductive current through the tip, either for pacing the heart or measuring blood impedance, most of the sensed impedance changes are local effects of the electrode-electrolyte interface. This electrolytic phenomenon occurs in all types of leads, bipolar as well as unipolar.

It will be recalled that the '725 pacemaker generates a measuring current between the ring electrode and the case but measures the blood impedance from a separate electrode, the tip electrode, which is located generally outside the vicinity of the electrolyte polarization arising from the applied measuring current. In the case of a pacemaker which uses a unipolar electrode, on the other hand, the measuring electrode and the current generating electrode are one and the same, and the measuring electrode is located precisely at the point of electrolyte polarization. Furthermore, the electrode tip has a very small surface area, over which the current is concentrated, leading to very large impedance changes where the electrode meets the electrolytes. Therefore, instead of measuring blood impedance as intended, a unipolar electrode constrains the pacemaker to predominantly detect the electrode-electrolyte polarization effects.

One method for reducing the problem of the electrode-electrolyte polarization effect is taught in U.S. Pat. No. 5,197,467, entitled "Multiple Parameter Rate-Responsive Cardiac Stimulation Apparatus" (hereinafter called the "'467 pacemaker"), issued Mar. 30, 1993 to B. M. Steinhaus et al., in which a metabolic demand rate-responsive cardiac stimulation apparatus and method are disclosed which employ multiple physiological rate control parameters, such as respiratory minute volume, patient motion and cardiac stroke volume. The parameters are derived using a single standard pacing lead or transducer. The '467 pacer performs each physiological measurement by periodically applying a measuring current between two points. This measuring current has frequency components in a range of from approximately 10 kilohertz to 1000 megahertz. Application of this measuring current allows the pacer to detect the voltage arising from the applied current and, from the detected voltage, to measure the patient's spatial impedance. The pacemaker reduces the problem of the electrode-electrolyte polarization effect by elevating the frequency content of the measuring electrical current much higher than the frequency employed in prior art impedance measuring devices. By elevating the interrogation frequency, the nature of the measuring current changes from a conduction current to predominantly a displacement current. At high frequencies a pacemaker lead can be viewed as a leaky conductor, or signal radiator. At higher measuring frequencies, more of the signal leaks from the lead throughout its length. The lead will measure the spatial impedance of the medium surrounding the lead. This is different from the measurement of "blood impedance", by means of interrogation using conduction current, as was performed in the '253 and '725 pacemakers. The '467 pacemaker performs the measurement through the length of the lead, not at the tip electrode. The tip electrode is separated from the input to the lead by the resistance, inductance and distributed capacitance of the lead. At higher measuring frequencies, these components of the lead impedance cause the flow of current along the lead to induce displacement currents in the tissue. Once the signal leaves the electrode tip, the current becomes a conduction current, creating the ionic conditions which make up the electrode-electrolyte polarization effect. The higher measuring current frequencies of the pacer greatly reduce the electrode-electrolyte polarization effect. The high frequency measuring current creates a displacement current within the body with little net current being injected into the body. The pacemaker creates this displacement current by generating an electrical current flowing within the conductor of the lead. This conductor is separated from the patient's body and its electrolytes by a layer of electrical insulation at the outside surface of the lead. The current within the lead generates an electrical field and creates the displacement current in the body.

Upon the generation of this coupled ionic field, a displacement current arises in the body, allowing the '467 pacer to detect impedance changes in the body remote from the location in which electrode-electrolyte artifacts arise. In this manner the pacer reduces the impedance effects of the tip electrode. The high frequency measuring current radiates more energy into the body along the lead and less to the tip, to reduce local artifact effects and inject less current into the heart. The reduction of local artifact effects greatly improves the signal quality of the measurement.

The present invention incorporates a sensor and sensing method that fundamentally differs from the method for reducing the problem of the electrode-electrolyte polarization effect taught in the '467 patent. The present invention employs a time domain reflectometer (TDR) for sensing a patient's body impedance. TDR systems have conventionally been used for testing communication cable integrity in transmission networks (see U.S. Pat. No. 4,970,466 to D. C. Bolles et al.). In another application TDR systems have been employed for testing for fluid leakage from underground storage tanks (see U.S. Pat. No. 5,134,377 to W. J. Reddy, III, et al.). TDR systems have not been used previously for impedance sensing in the cardiovascular system. Additionally, TDR systems have not been used previously for sensing physiologically-varying parameters in the body.

A conventional time domain reflectometer (TDR) measures network impedance as a function of time or distance. It does this by generating a voltage step at the input to a transmission line and measuring the change in voltage at the line input due to reflections from impedance discontinuities along the line. The shape of the sensed voltage waveform arising in response to the leading edge of the interrogating pulse is related to the impedance as a function of distance down the lead. Impedance changes along the lead in the path of the pulse reflect voltages back to the line input. These impedance changes determine the amplitude and phase of the reflections. In turn, the reflections add or subtract to the pulse voltage at the input, thereby changing the morphology of the waveform. Conventional TDR systems are used for network analysis to diagnose faults in coaxial and fiber optic cables and to characterize interconnect nodes in hybrid circuits. These TDR systems generally consist of a voltage step generator and an oscilloscope. The TDR voltage step generator sends a voltage pulse with a very fast rise time on its leading edge down the transmission line and the oscilloscope then measures the voltage at the input to the line. The reflections appear at the transmission line input, superimposed on the input voltage from the step generator at a time delayed from the beginning of the rising edge of the step input. This time delay is twice the propagation time to the location of an impedance discontinuity along the transmission line. The principle of operation in TDR is similar to that of radar, the time of flight of the edge down and back up the lead indicates the distance to the reflection.

In conventional TDR systems for analysis of transmission networks using coaxial cables, signals and reflections propagate in a medium consisting of the dielectrical filler between the inner and outer conductors of the cable. In the TDR system of the present invention, the signal travels along an implantable lead or catheter in which the medium of propagation is the tissue surrounding the lead.

The present invention is utilized to measure the impedance of a patient-implanted lead or catheter in order to derive information reflecting both the patient's physiological functions and the condition of the lead or catheter.

The present invention performs this measurement using time domain reflectometry in which a voltage pulse, having the general form of a step or pulse function, is applied to the lead or catheter. The lead or catheter is then monitored to detect reflections superimposed on the applied voltage pulse. These reflections are indicative of impedance variations both along and distal to the lead or catheter.

Further objects and advantages of the invention will become apparent as the following description proceeds.

SUMMARY OF THE OF THE INVENTION

Briefly stated, and in accordance with one embodiment of the present invention, a sensor in a medical device is provided for measuring a patient's internal body impedance. The sensor includes a transmission line implanted in the patient's body tissue. This transmission line may be in the form of a pacing lead, a defibrillator lead, a catheter, an antenna coil or other electrically conductive material that may be implanted within the patient's tissue. The sensor also includes means for applying an electrical stimulation to the implanted transmission line to propagate the electrical stimulation through the patient's tissue. The stimulation applying means may be in the form of a switched capacitor circuit, a function generator, a pulse generator, a signal generator, a step generator, a step recovery diode, an electrostatic discharge circuit or other device for generating an electrical step, pulse or impulse function of voltage or current. The sensor also includes means for measuring a reflected electrical signal from the implanted transmission line that results due to reflections of the propagated electrical stimulation as it encounters impedance variations in the patient's tissue. The measuring means may be in the form of a switched capacitor circuit, an oscilloscope, a digitizing oscilloscope, a sample and hold circuit or other electrical signal measuring device. The sensor further includes means for deriving an impedance signal as a function of the reflected electrical signal. The deriving means may take the form of a controller, a microprocessor, a microcomputer, a computer, a data recorder or a data sampler.

In accordance with a second embodiment of the present invention, the elements of the aforesaid first embodiment may be further combined with means for distinguishing electrical signals arising within at least one predetermined time interval of the time-varying reflected electrical signal from electrical signals arising outside such an interval. The distinguishing means may be a controller in combination with a timing circuit, for selecting both a predetermined delay interval following the time of delivery of the stimulation pulse and a sampling interval, and for sampling the electrical signal during the sampling interval. Alternatively, the distinguishing means may take the form of circuits, discussed hereinafter, that emphasize signals occurring during particular time intervals following the stimulation delivery. The sensor of this second embodiment of the invention also includes means for deriving an impedance signal as a function of the distinguished electrical signals.

In accordance with a third embodiment of the present invention, a sensor in a medical device is provided for measuring a patient's internal body impedance. The sensor includes a lead implanted in the patient's blood vessels, extending from a proximal end to a distal end. A pulse generator is coupled to the implanted lead at its proximal end and, upon request, applies a voltage pulse to the lead. The sensor further includes means for measuring a reflection voltage waveform on the implanted lead that results from reflections of the applied voltage pulse due to impedance variations arising along the lead. These impedance variations arise not only along the lead but also extend beyond the distal tip of the lead into the patients blood vessels and heart chambers. The sensor additionally includes means for deriving an impedance signal as a function of the measured reflection voltage waveform.

In accordance with a fourth embodiment of the present invention, a sensor measures a patient's internal body impedance. A lead, extending from a proximal end to a distal end, is implanted in the patient's blood vessels and heart chambers. The proximal end of the lead is coupled to a pulse generator, which applies a voltage pulse to the lead. The application of the voltage pulse starts a timer for timing a predetermined delay interval and, at the end of the delay interval, timing a predetermined sample duration interval. Upon termination of the predetermined delay interval and enduring until termination of the sample duration interval, a means for measuring a reflection voltage waveform on the implanted lead is provided. The reflection voltage waveform results from reflections of the applied voltage pulse from impedance variations arising along the lead and extending distally beyond the lead's distal tip into the patient's blood vessels and heart chambers. The aforementioned delay interval and sample duration interval are predetermined to select a range of distance from the proximal end of the lead. The sensor further includes means for deriving a range-selected impedance signal as a function of the reflection voltage waveform.

This fourth embodiment of the invention may further include means for repetitively triggering the pulse generator while maintaining the predetermined delay interval and the predetermined sample duration interval constant. The range-selected impedance signals resulting from the repetitive triggering are arranged into a time-varying range-selected impedance signal.

In accordance with a fifth embodiment of the present invention, the aforementioned sensor embodiments may be incorporated into a system for testing a pacing electrode in an implantable cardiac pacemaker.

In accordance with a sixth embodiment of the present invention, the aforementioned sensor embodiments may be incorporated into an implantable cardiac pacemaker which is adapted for measuring physiological parameters such as respiration and heart motion for diagnostic or therapeutic purposes.

BRIEF DESCRIPTION OF THE DRAWINGS

While the specification concludes with claims particularly pointing out and distinctly claiming the subject matter of the invention, it is believed that the invention will be better understood from the following detailed description, taken in conjunction with the accompanying drawings, in which:

FIG. 10 is a graphical, three-dimensional depiction of sequential, simulated TDR waveforms;

FIGS. 11A and 11B depict, respectively, simulated graphs of a TDR voltage waveform and a respiration waveform derived from voltage measurements made during corresponding selected windows of many sequential TDR voltage waveforms.

DETAILED DESCRIPTION

Figure 1:
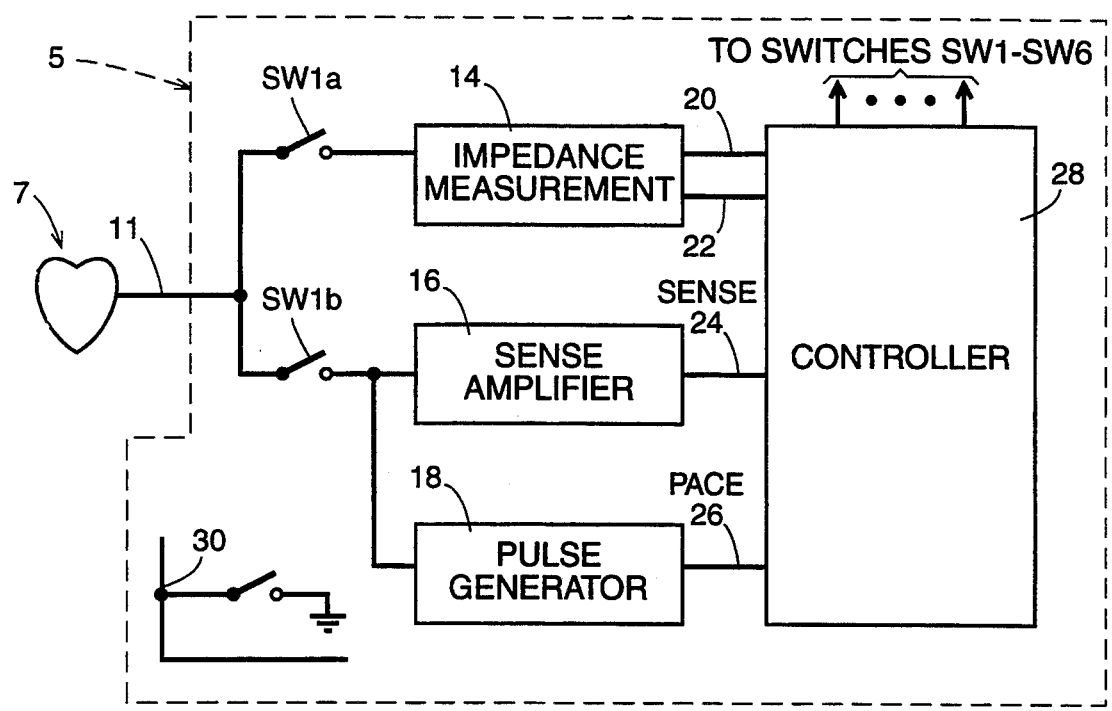
FIG. 1 is a block diagram of an illustrative embodiment of the invention, a TDR impedance sensor, incorporated in a cardiac pacemaker.

Referring to of FIG. 1, a high-level block schematic of a pacemaker is shown generally at 5. Although the invention, an impedance sensor, is described herein as part of a cardiac pacemaker, it may also be employed in defibrillators, cardioverters, antitachycardia pacemakers, electrophysiology test systems, implantable holter monitors and other similar medical diagnosis and therapeutic devices. The impedance sensor of the present invention may be employed in conjunction with pacing leads, defibrillator leads, catheters, antenna coils and other electrical conductors that are capable of serving as a transmission line. These transmission lines may be permanently or temporarily inserted into the cardiovascular system for diagnostic and therapeutic purposes. All logic employed in pacemaker 5 is under the control of a controller 28 (which may include a microprocessor). The controller 28 operates various switches in the pacemaker 5, of which only one pair SW1A, SW1B is shown. Switch SW1B is closed whenever the pacemaker 5 is to pace or sense.

Figure 2:
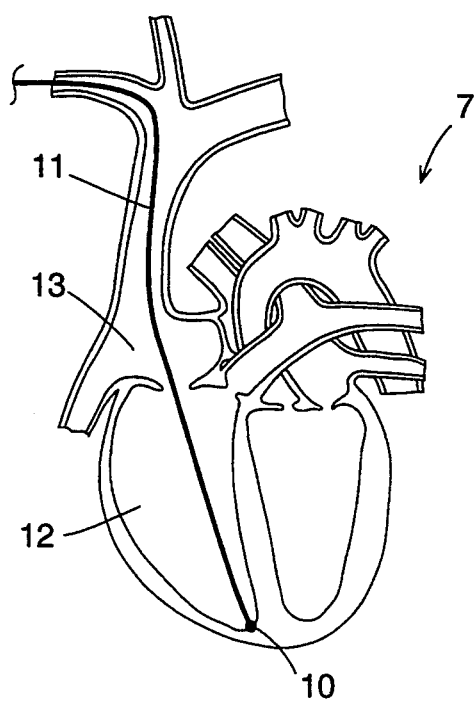
FIG. 2 depicts placement in a patient's right ventricle of a lead which may be used both to perform TDR impedance measurements and to perform pacing and sensing.

Referring to FIGS. 1 and 2, together, in order to pace, the controller 28 sends a command to a pulse generator 18 by means of a signal on a PACE conductor 26. The pulse generator 18 responds to this command by applying a current pulse through the switch SW1B and a conventional unipolar, bipolar or multipolar lead 11 to the latter's tip electrode 10, which is shown positioned in the right ventricle 12 of a patient's heart 7 in FIG. 2. The term "lead" is used generically herein and is intended to include catheters, wires and conductors of any type capable of freely conducting an electrical voltage or current therein. A sense amplifier 16 senses a cardiac signal on the electrode. (Various functions well known in the art, such as blanking of the sense amplifier during pacing, are not shown inasmuch as they have no bearing on the subject invention.) The sensing of a heartbeat, spontaneous or evoked, results in a pulse appearing on SENSE conductor 24 and being delivered to controller 28.

The pacemaker 5 makes an impedance measurement when the controller 28 pulses a conductor 20 to activate a time domain reflectometer or TDR impedance sensor circuit 14. Upon this event, switch SW1A closes and switch SW1B opens and TDR impedance sensor circuit 14 applies a voltage to the lead The voltage quickly propagates down the lead 11 toward the tip electrode 10. The measuring voltage applied to the lead 11 is in the form of a step or pulse function having a preset width. As the rising edge of the voltage step or pulse propagates down the lead 11 any impedance variations along the lead 11, both within the lead itself (due to breakage, for example) or in the surrounding tissue, result in a voltage perturbation which reflects back to the pacemaker 5. The TDR impedance sensor circuit 14 measures spatial impedance by determining the potential difference between the pacemaker case 30 and the pacemaker input connection to the conductor (not shown) within lead 11. This potential difference is the additive composition of the applied step or pulse function voltage and voltages arising from reflections from impedance variations. The conductor extends to the tip electrode 10. In this configuration, the pacemaker case 30 serves as a reference potential for the pacemaker circuitry. In the preferred embodiment of the pacemaker 5, the TDR impedance sensor circuit 14 derives samples at a rate appropriate for the type of information sought in performing the measurement and communicates these samples to controller 28 over output bus 22. (For example, if impedance signals are used to measure patient respiration, a sample rate of about 20 per second is appropriate. If heart motion is measured, a rate of approximately 200 Hz is required.)

Placement of a pacing lead, either unipolar or bipolar, is shown in FIG. 2. The tip electrode 10 makes contact with the wall of the right ventricle 12 or the right atrium 13 of the patient's heart 7. When the TDR impedance sensor circuit 14 generates a measuring voltage step, as will be described hereinafter, the impedance measurement is characteristic of physical impedance phenomena in positions along the lead 11. After application of the voltage step, the first voltage reflections measured by the impedance sensor 14 indicate impedance variations most proximal on the lead. Later voltage reflections arise from impedance variations that are more distal on the lead 11. Additional reflections are sensed later in time, corresponding to impedance changes all the way to the tip electrode 10 of the lead 11 and beyond. Voltage reflections sensed beyond the tip electrode 10 result from impedance variations distal to the lead 11, within the patient's blood vessels and heart chambers. The blood vessels and heart chambers act as an extension of the lead 11 (due to their conductivity) and their impedance variations are reflected back along the lead 11. This phenomena, graphically shown hereinafter and discussed with regard to FIGS. 9, 10, 11A, 11B, 12A and 12B, is important since it provides for sensing of additional physiological phenomena. For example, at various locations along the lead 11 and beyond, impedance variations arising from patient respiration may predominate. In other locations, near the distal portion of the lead 11 and beyond, impedance changes are characteristic of heart motion. The sensing of impedance signals may be controlled to select impedance changes arising from one or more particular physiological phenomena by selecting a time window subsequent to a delay which follows the applied voltage step or pulse, for measuring each type of signal.

Figure 3:
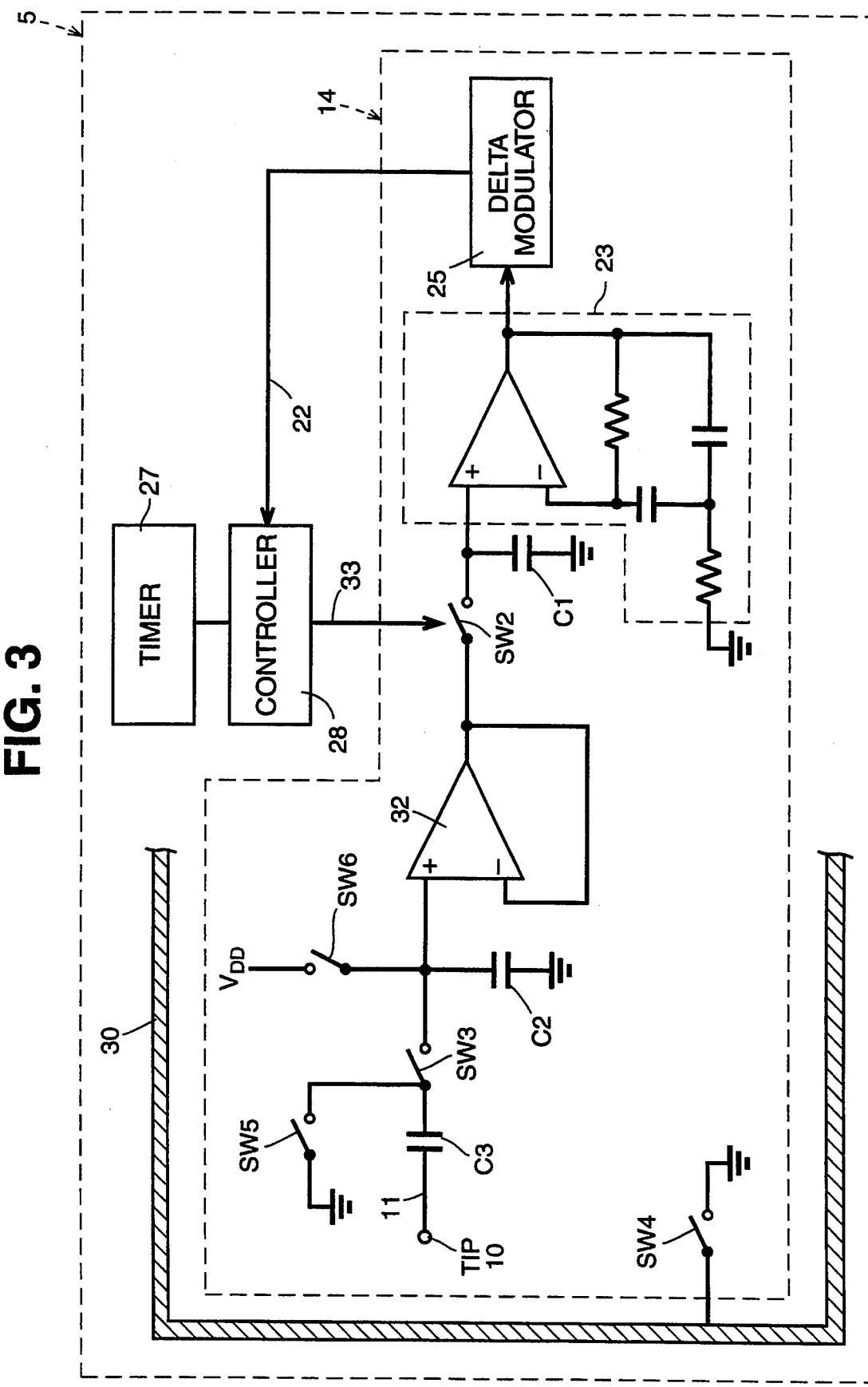
FIG. 3 depicts an embodiment of a TDR impedance sensor circuit, shown in block form in FIG. 1, which employs highspeed switches in its operation.

Referring to FIG. 3, an embodiment of the TDR impedance sensor circuit 14 adapted for operation in a time domain reflectometry (TDR) mode is shown. The TDR impedance sensor circuit 14 includes a connection through a switch SW4 to the case 30, and a connection through a switch SW3 to the tip electrode 10 (via the pacing lead 11). The tip electrode 10 is a conventional pacing/sensing electrode. The indifferent electrode is the case 30. The TDR impedance sensor circuit 14 employs the tip electrode 10 and lead 11 both for applying a voltage step or pulse to the patient's body, and for measuring voltage reflections returning from the lead 11 that result from the applied voltage step. A buffer amplifier 32 and filter 23 are also employed in circuit 14.

All switches in FIG. 3 are directly or indirectly under the control of controller 28. One output 33 of the controller is shown extending to switch SW2, but it is to be understood that switches SW3, SW4, SW5 and SW6 are similarly controlled. The controller closes switch SW6 to charge a measuring capacitor C2 to a regulated voltage source V00- Subsequently, the controller opens switch SW6 and closes switches SW3 and SW4 while switch 8W5 is held open, thereby connecting measuring capacitor C2 to lead 11 through a coupling capacitor C3. While the switches SW3 and SW4 are closed, measuring capacitor C2 discharges through capacitor C3 into the lead 11, thereby applying the voltage that is across measuring capacitor C2 to the lead 11. To provide TDR measurements, the circuit of FIG. 3 generates periodic interrogating voltage pulses and senses echoed (reflected) signals superimposed on the interrogating pulses. The interrogating voltage pulses preferably are pulses. generated in the form of 2 volt amplitude, 1 $\mu$s wide pulses occurring at 50 ms intervals, although voltage pulses in the form of a step function having an amplitude in the range of from 1 $\mu$V to 100 $\mu$V, a pulse width in the range of from 1 ns to 5 ms and a pulse repetition rate in the range of from 0.1 Hz to 500 Hz may be employed. The controller 28 is coupled to a timer 27. The controller 28 commands the timer 27 to generate periodic timing signals. The timer 27 generates appropriate timing signals and notifies the controller 28 when a requested time interval expires. The output 33 controls switches SW2, SW3 and SW4 so that a single command from the controller 28 closes, then opens, all three switches. Switches SW3 and SW4 are closed first, essentially simultaneously, and switch SW2 is closed shortly thereafter, following a predetermined sampling delay, ranging in duration from approximately 1 to 200 nanoseconds.

The closing of switches SW3 and SW4 allows the buffer amplifier 32 to access the voltage held on the measuring capacitor C2. This voltage is advanced through the buffer amplifier 32 and through switch SW2, which switch is closed at the end of the aforesaid predetermined sampling delay which follows the opening of switches SW3 and SW4, and is sampled on capacitor C1 at the input of the filter 23. A single command from the controller 28 controls switches SW2, SW3 and SW4 because the response time of the controller 28 would be too slow to sense the time of flight reflections if separate commands were to be used to operate the switches. The switch SW2 is closed for a sampling or measuring time interval having a preset duration $\Delta T$, during which the combined interrogation voltage step and superimposed reflection signal are sampled. The sampling interval $\Delta T$ may range from about 10 to 200 nanoseconds.

During the sampling interval, the amount by which the voltage across measuring capacitor C2 changes depends on impedance variations along the lead 11 and the voltage reflections created by these impedance variations. Measuring capacitor C2 stores the voltage and buffer amplifier 32 transfers this measurement to the filter 23. Following the predetermined measuring time interval $\Delta T$, switches SW2, SW3 and SW4 are opened. The opening of switches SW3 and SW4 may occur somewhat after the opening of switch SW2. For example, the duration of the interrogating voltage pulses, as controlled by switches SW3 and SW4, may be 1 $\mu$s, regardless of the duration of the sampling interval determined by switch SW2.

The controller 28 then closes switch SW6 to charge measuring capacitor C2 for the next measuring cycle measurement. In the preferred embodiment of the invention, the controller 28 measures impedance twenty times per second, at 50 ms intervals. For each measurement, the controller 28 closes the switches SW3 and SW4 for a pulse duration of 1 $\mu$s, during which the voltage across the capacitor C2 is placed on the lead 11.

The value of the measuring capacitor C2 is selected to store the range of voltages which result- from various body impedances. In one embodiment of the invention, C2 has a capacitance of 4.7 nF. The coupling capacitor C3 provides for DC isolation for the input to the measuring circuit.

The resistors and capacitors associated with filter 23 are selected to pass various signal frequencies, depending on the type of signal to be analyzed. It was hereinbefore stated that the sensing of impedance signals may be controlled to select impedance changes arising from one or more particular physiological phenomena by selecting a time window following the applied voltage step or pulse for each type of signal. The selection of sampling time windows, and the values of the resistors and capacitors associated with filter 23, are preferably selected in a coordinated manner to provide for good signal fidelity with respect to a particular physiological parameter. In an embodiment of the invention selected to measure respiratory signals, the impedance signal is filtered by a two-pole filter with a center frequency of 0.2 Hz. The gain is reduced by a factor of two (6 dB) at frequencies of 0.05 Hz and 0.8 Hz. The cutoff frequencies for a bandpass filter that favors cardiac motion signals may range from 0.2 to 10 Hz.

The analog signal output of the filter 23 passes to a delta modulator 25 which provides a digital signal output on output bus 22. The digital signal output on output bus 22 is input to the controller 28 for processing. Converting an analog signal to a digital representation by delta modulation is a standard technique. One example of such an operation is illustrated in U.S. Pat. No. 4,692,719 to Robert H. Whigham, entitled "Combined Pacemaker Delta Modulator and Bandpass Filter", which issued on Sep. 8, 1987. The output of the delta modulator 25 is a summation of a series of 0's and 1's which reflect whether the analog signal is decreasing or increasing.

During a measurement interval, controller 28 opens switch SW1B (shown in FIG. 1) to briefly disable pace and sense functions. Although sensing is disabled while the impedance measurement is in operation, the duration of the measurement is on the order of fractions of microseconds, a time so short relative to that of heart signals that disabling sensing during this time is of no importance.

Although the sensor circuit 14 depicted in FIG. 3 is used in a pacemaker 5, it is intended that the impedance sensor may be used in other implantable devices such as defibrillators and antitachycardia pacers. Furthermore, it is intended that the impedance sensor of the present invention may be employed in a device that, except for the lead or catheter, is not implanted or implantable but rather is positioned external to a patient and coupled to a catheter or lead, which is inserted into the patient's body. For example, it may be used with a catheter that is temporarily inserted into the cardiovascular system for diagnostic purposes. In another application, the external impedance sensor may be coupled to an implanted pacing lead and impedance may be sensed to determine whether the lead may have any breaks or imperfections. Such breaks or imperfections give rise to impedance variations or discontinuities in the sensed impedance waveform.

Figure 4A:
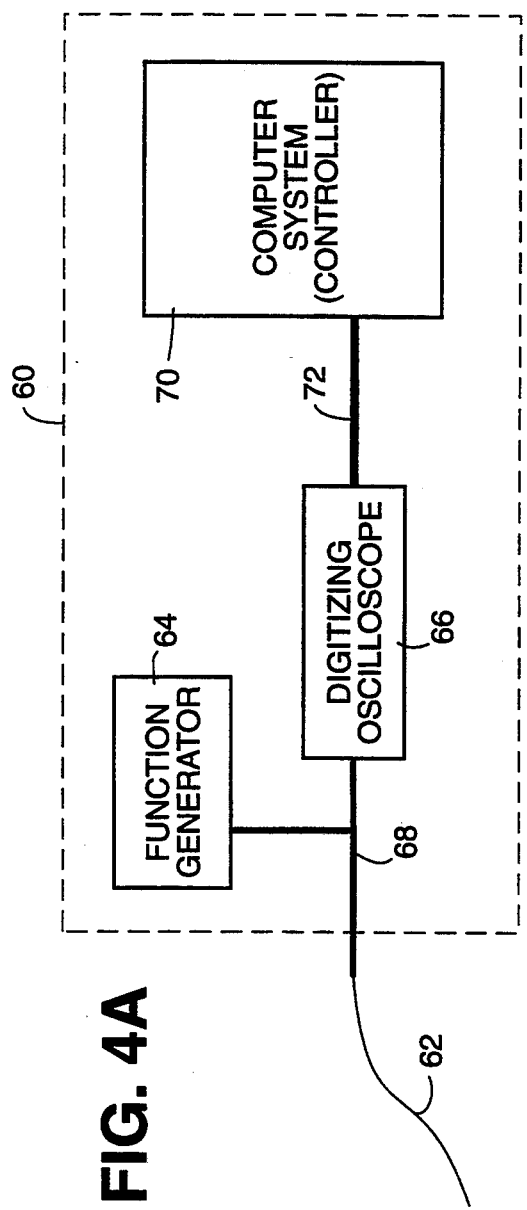
FIGS. 4A and 4B illustrate embodiments of a TDR impedance sensor which are adapted to sense the impedance of transmission lines in the forms of, respectively, a catheter or lead on one hand, and alternatively, an antenna coil.
Figure 4B:
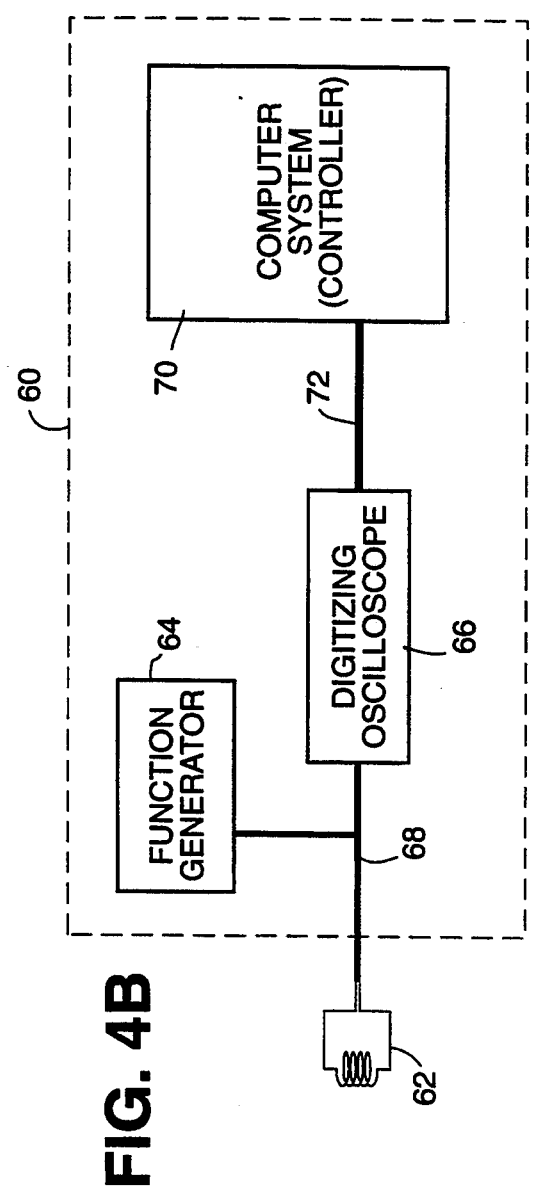

One example of an impedance sensor that is external to the patient, rather than implantable, is illustrated generally at 60 in FIGS. 4A and 4B. The impedance sensor 60 of FIG. 4A drives a transmission line 62 (e.g., a subcutaneous catheter) and includes means for applying an electrical stimulation 64 (e.g., a pulse generator or function generator) coupled to a means 66 for measuring electrical signals (e.g., a digitizing oscilloscope) via a transmission line 68 (e.g., a coaxial cable). In this example, the digitizing oscilloscope 66 is controlled by a controller 70 (e.g., a computer system), which is coupled to the oscilloscope 66 by an interface 72. The function generator 64, for example an Hewlett-Packard HP 3314A TM function generator (made by Hewlett-Packard Company, 3000 Hanover Street, Palo Alto, Calif. 94304, USA), generates pulses at a predetermined amplitude, pulse width and frequency. In an exemplary embodiment of the invention, the function generator 64 may provide 2 volt, 1 μs width pulses at a frequency of 20 Hz (50 ms intervals). Pulses may be generated equivalently by other electrical stimulation applying means which are known in the art, such as switched-capacitor circuits, step recovery diodes, electrostatic discharge circuits, signal generators, pulse generators and step generators. For each pulse of the function generator 64, the computer system 70 (e.g., Toshiba 100 TM laptop computer, made by Kabushiki Kaisha Toshiba D/B/A Toshiba Corporation, 72, Horikawa-Cho, Saiwai-Ku, Kawasaki-Shi, Kanagawa-Ken, Japan), in response to a trigger by the function generator 64, initiates data acquisition by commanding the digitizing oscilloscope 66 (e.g., Hewlett-Packard HP 54510A TM, made by Hewlett-Packard Company, 3000 Hanover Street, Palo Alto, Calif. 94304, USA) to acquire a preset number of waveform samples (e.g., 100) until a predetermined number of waveforms (e.g., 200), each comprising such preset number of samples, are acquired. For example, 10 seconds of data may result from each data acquisition. Each waveform may contain 100 samples, spaced at the oscilloscope 66 sample rate of one sample per nanosecond. The oscilloscope 66 may store the waveform in its internal memory (not shown) until all the data is acquired. Waveforms may be measured equivalently by other devices which are known in the art, such as switched-capacitor circuits, sample and hold circuits and oscilloscopes. Data may be transferred to the computer 70 over the interface 72 (e.g. National Instruments AT-GPIB IEEE-488 TM interface, made by National Instruments Corporation, Austin, Tex., USA). The computer system 70 analyzes the data to derive an impedance waveform. Data may be analyzed equivalently by other devices which are known in the art, such as controllers, microprocessors, microcomputers, data recorders and data samplers.

In another example of an impedance sensor 60 that may also be depicted by the block diagram of FIG. 4A, in this case a fully implantable impedance sensor, the sensor 60 drives a transmission line 62 in the form of an implanted pacing lead. The impedance sensor 60 again includes a means 64 for applying an electrical stimulation, which in this case may be a switched capacitor circuit, a step recovery diode, an electrostatic discharge circuit or other form of pulse generator. The electrical stimulation applying means 64 may generate electrical stimuli in the form of step voltage stimuli, step current stimuli, pulse voltage stimuli or pulse current stimuli. These stimuli must have a sufficiently fast rise time to allow discrimination of impedance variations along the transmission line 62. (The faster the rise time of stimulation applying means 64, the better the discrimination of impedance variations along the transmission line 62.) The electrical stimulation applying means is sufficiently low in current drain and small in size to provide for efficient generation of stimulating pulses for years. As in the previous example, the electrical stimulation applying means 64 is coupled to an electrical signal measuring means 66, for example a data acquisition, a sample and hold or a data sampling circuit, and the electrical signal measuring means 66 is controlled by a controller 70. The controller 70 directs the electrical stimulation applying means 64 to generate pulses at a predetermined amplitude, pulse width and frequency. For example, the electrical stimulation applying means 64 may provide 2 volt, 1 μs width pulses at a frequency of 20 Hz (50 ms intervals).

For each pulse of the electrical stimulation applying means 64, the controller 70, in response to a trigger by the electrical stimulation applying means 64, may command the electrical signal measuring means 66 to acquire a sample "TDR" waveform of the electrical signal reflected due to the application of the electrical stimulus. The electrical signal measuring means 66 then samples the electrical signal on the pacing lead 62. The round trip time of flight of reflected echoes, and variations in their signal level, are indicative of the location and types of impedance discontinuities that occur along the pacing lead 62. Thus, the impedance sensor 60 may be employed to test the pacing lead 62 for breaks or imperfections.

In addition to usage in testing the pacing lead 62 the impedance sensor 60 may be utilized to measure physiological parameters, such as respiration and heart motion, by repeatedly triggering electrical stimulation pulses and impedance measurements. For each pulse of the electrical stimulation applying means 64, the controller 70, in response to a trigger by the electrical stimulation applying means 64, may command the electrical signal measuring means 66 to acquire a TDR waveform of the electrical signal reflected as a result of the application of the electrical stimulus. The electrical signal measuring means 66 then samples the electrical signal on the pacing lead 62. The round trip times of flight of reflected echoes are indicative of the positions of impedance variations both along the pacing lead 62 and beyond the tip of the lead 62. The controller 70 commands the acquisition of a preset number of TDR waveform samples until a predetermined number of waveforms are acquired. By analyzing changes that occur in the signal levels during corresponding time windows of the TDR waveform samples, the impedance sensor 60 may be employed to measure physiological parameters for usage in pacing therapy or diagnostic procedures, as will appear in greater detail hereinafter.

A further example of an impedance sensor is depicted by the block diagram of FIG. 4B. In this case the impedance sensor functions in the same manner as the impedance sensor 60 of FIG. 4A but a coil antenna replaces the lead or catheter of that figure as the transmission line 62. The embodiment of the invention in FIG. 4B is useful for measuring physiological function in an implantable holter monitor device.

Figure 5:
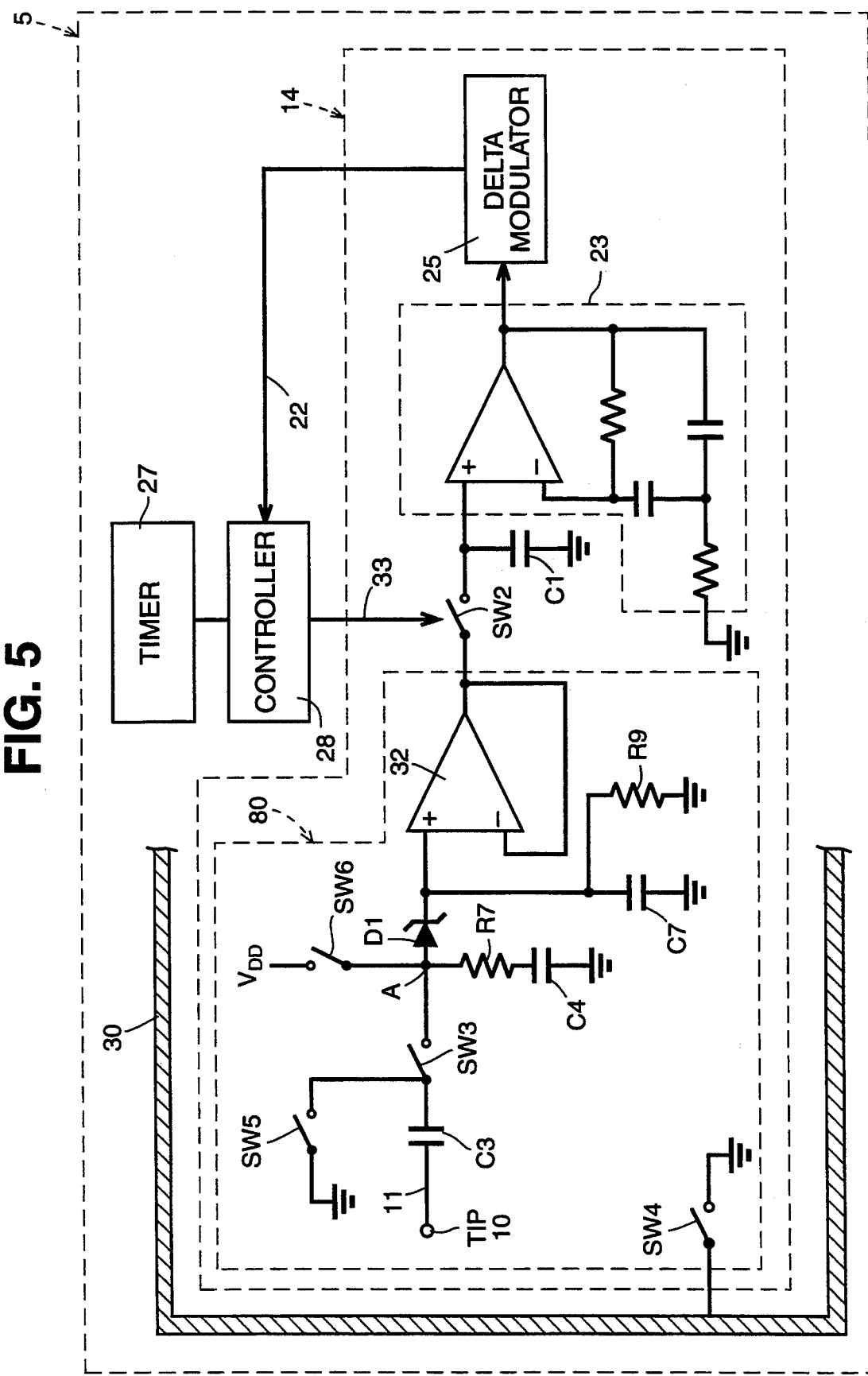
FIG. 5 depicts an embodiment of a TDR impedance sensor circuit, shown in block form in FIG. 1, which employs a constant voltage circuit in its operation.
Figure 7:
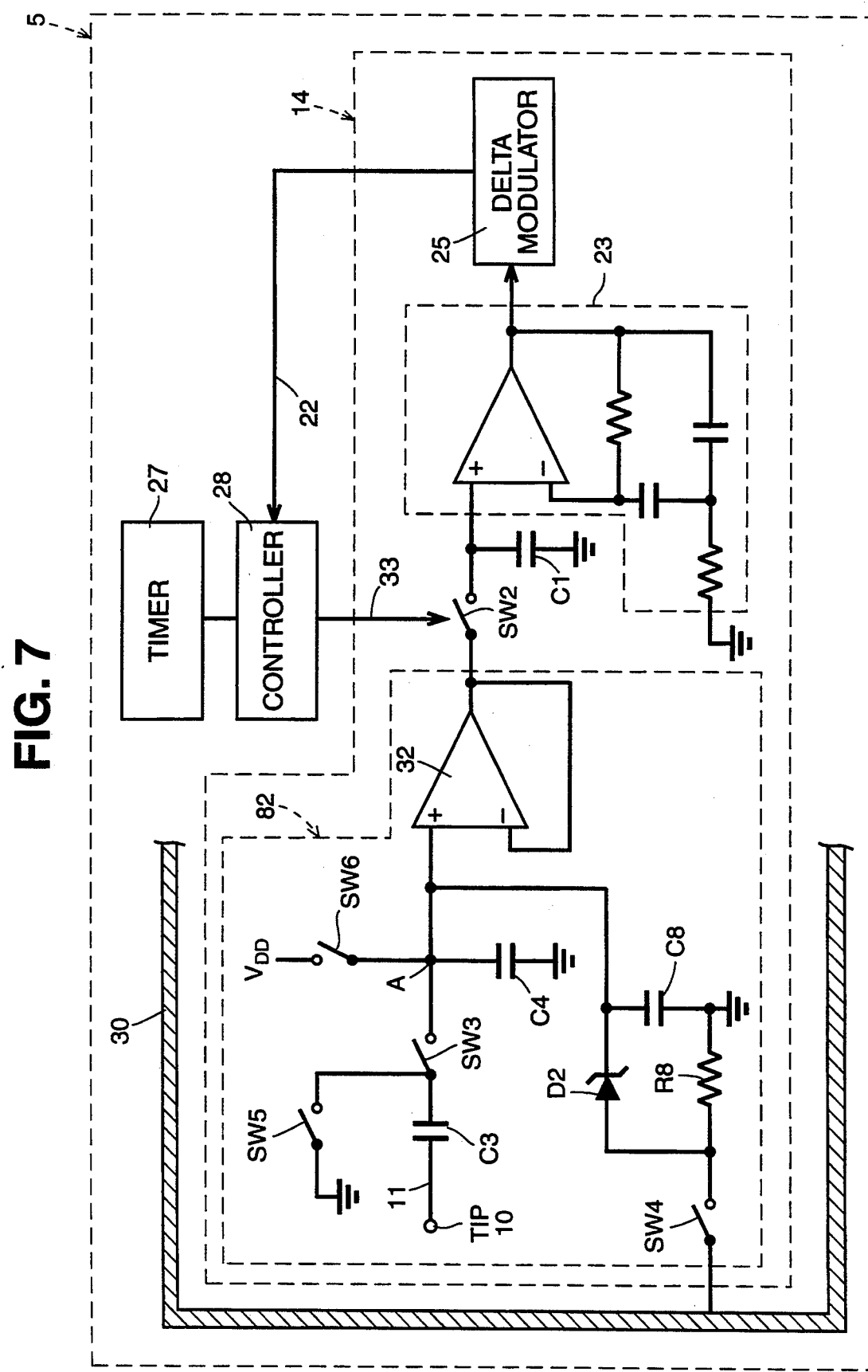
FIG. 7 depicts an embodiment of a TDR impedance sensor circuit, shown in block form in FIG. 1, which employs a peak current circuit in its operation.

One of the advantages of the time domain reflectometer (TDR) impedance sensor is its ability to measure impedance changes arising from a particular physiological function. This capability requires very fast operation of switches, such as those shown in the TDR impedance sensor circuit 14 of FIG. 3, or a high speed digital oscilloscope, similar to that illustrated in FIG. 4A. Such a high speed switching operation is difficult to achieve in an implantable pacemaker or defibrillator due to its inherent high energy requirements. FIGS. 5 and 7 illustrate impedance measurement circuit embodiments that are adapted to sense impedance variations at selected intervals along the lead and beyond, but do not require high speed switching. These circuit embodiments are called a constant voltage circuit (FIG. 5) and a peak current circuit (FIG. 7).

FIG. 5 depicts a TDR impedance sensor circuit 14 which employs a constant voltage circuit 80 and is adapted for operation in a time domain reflectometry (TDR) mode. The constant voltage circuit 80 takes the form of a voltage divider that has a step voltage pulse applied to a network therein consisting of impedance elements connected in series. The DC voltage that results from the applied voltage pulse is measured at a point between the impedances. The constant voltage circuit 80 generates a step voltage change, followed by an essentially constant voltage at the input to the lead 11, then measures impedance changes in relationship to time after the generation of the voltage step. The circuit 80 measures the combined interrogating and reflected voltage waveforms while the voltage input is applied to the lead The constant voltage circuit 80 includes switches SW3, SW5 and SW6 for connecting, respectively, the lead 11 (through coupling capacitor C3), reference ground and the regulated voltage source $V_{DD}$ to a node A in the circuit 80. Switch SW4 connects reference ground to the pacemaker case 30. Node A is coupled to the positive input of the buffer amplifier Switches SW3, SW4, SW5 and SW6, tip electrode 10, lead 11, case 30, regulated voltage source $V_{DD}$, coupling capacitor C3 and buffer amplifier 32 of the constant voltage circuit 80 of FIG. 5 are functionally and structurally equivalent to like-named components of FIG. 3. In the constant voltage circuit 80, a step generator capacitor C4 replaces the measuring capacitor C2 of FIG. 3. In addition to the circuit elements of FIG. 3, the constant voltage circuit 80 includes a series resistor R7, a rectifier diode D1 and a constant voltage measuring capacitor C7. A resistor R9 provides a discharge path for measuring capacitor C7.

The constant voltage circuit 80 employs the tip electrode 10 and lead 11 both for applying a voltage step to the patient's body, and for measuring voltage reflections returning from the lead 11 that result from the applied voltage step. The controller closes switch SW6 to charge the step generator capacitor C4 to the regulated voltage source $V_{DD}$. Subsequently, the controller opens switch SW6 and closes switches SW3 and SW4 while switch SW5 is held open, thereby connecting the step generator capacitor C4 to lead 11 through a coupling capacitor C3. While the switches SW3 and SW4 are closed, step generator capacitor C4 discharges through capacitor C3 into the lead thereby applying the voltage across step generator capacitor C4 to the lead 11. As the step voltage is applied to the lead 11, the constant voltage circuit 80 performs as a voltage divider network consisting of two impedances, connected in series. A first impedance is the series resistor R7. A second impedance is the patient's body, which is coupled between the lead 11 (at tip electrode 10) and the case 30. The voltage at node A is measured on the constant voltage measuring capacitor C7, after passing through the rectifier diode D1, so that the largest voltage appearing at node A is measured during the step voltage application. In this manner, the constant voltage circuit 80 measures the voltage resulting from combination of the addition to the interrogating step voltage of reflected signals arising from impedance variations in the lead 11 and in the patient's body.

The constant voltage measuring capacitor C7 stores this resulting voltage, and buffer amplifier 32 later transfers this voltage to the filter 23. After a predetermined measuring time interval ΔT, the controller 28 opens switches SW3 and SW4, allowing the buffer amplifier 32 to access the voltage held on the constant voltage measuring capacitor C2. This voltage is advanced through the buffer amplifier 32 and through switch SW2, and is sampled on capacitor C1 at the input of the filter 23. For the next measuring cycle, the controller 28 opens switch SW2 and closes switch SW6 to charge the step generator capacitor C4 for the next measurement. In the preferred embodiment of the invention, the controller 28 measures impedance twenty times per second. For each measurement, the controller closes the switches SW3 and SW4 for a pulse duration of 1 us, during which time the step voltage is applied to the lead 11, reflection signals are echoed and superimposed on the step voltage and the measuring capacitor C7 is charged to the maximum value of the superimposed signal.

Figure 6A:
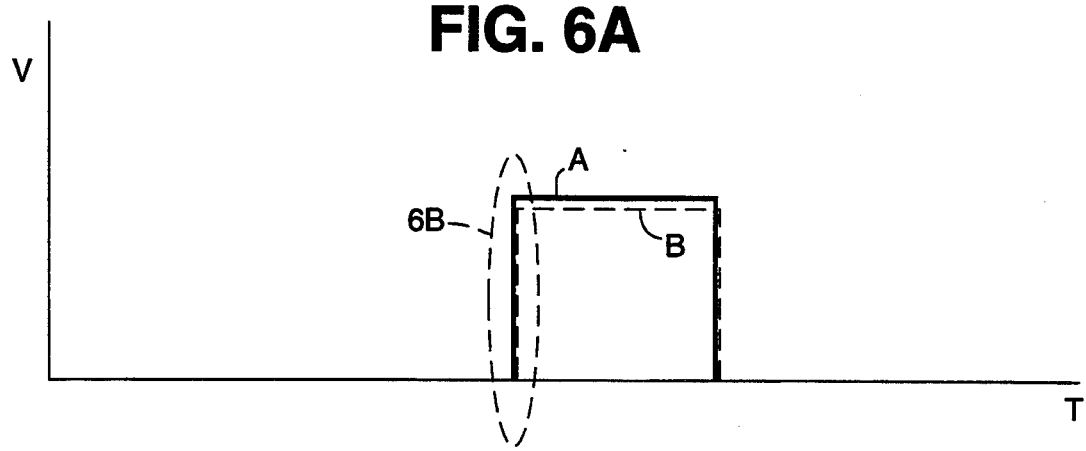
FIGS. 6A and 6B are graphical depictions of time waveforms, each illustrating a voltage step input applied to a lead and a measured response signal elicited by the input, measured by the constant voltage circuit of FIG. 5, wherein the FIG. 6B waveform illustrates the FIG. 6A waveform in time-expanded form.
Figure 6B:
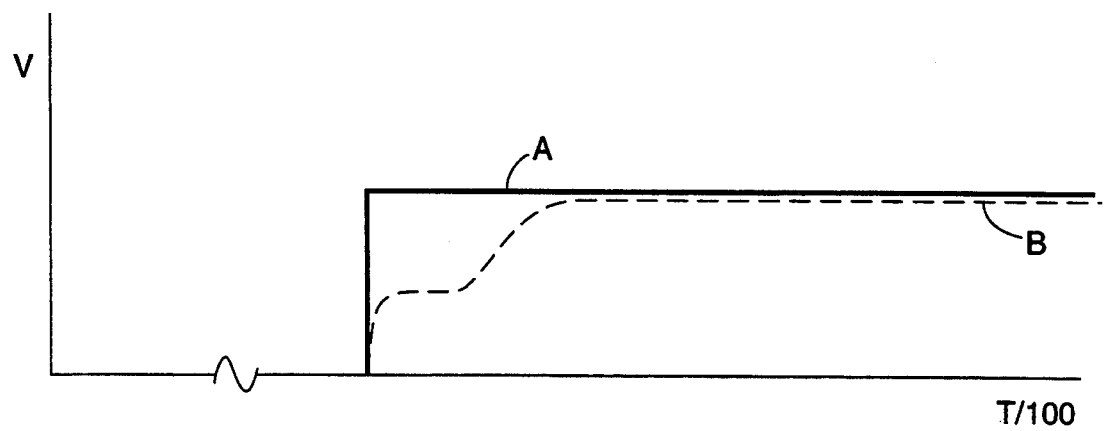

The purpose of the FIG. 5 (constant voltage circuit embodiment of the TDR impedance sensor 14 is to restrict the time of taking the impedance measurement to a particular portion of the measurement field, more precisely, the portion of the field which extends beyond the tip of the lead thereby to eliminate the need for high speed switches. The maximum signal amplitude arises from impedance characteristics lying beyond the distal end of the lead 11. For the application of a cardiac pacemaker 5 with the lead tip electrode implanted in a patient's heart, impedance signals arising beyond the distal end of the lead are a function of heart motion. FIGS. 6A and 6B are graphical depictions of an applied step voltage A and a voltage response B, as measured by the constant voltage circuit 80. For each waveform, the constant voltage circuit 80 determines only one value, the maximum impedance signal, which arises beyond the distal end of the lead 11.

FIG. 7 depicts a TDR impedance sensor circuit 14 which employs a peak current circuit 82 and is adapted for operation in a time domain reflectometry (TDR) mode. The peak current circuit 82 applies a step voltage pulse to a lead 11 through a peak current measuring resistance Re and measures the peak current flowing through the resistance. The peak current circuit 82 includes a rectifier diode D2 and a peak current measuring capacitance C8 across the resistance RS to measure and store the voltage proportional to the current flowing through the resistance RS. The peak current circuit 82 generates a step voltage change, followed by an essentially constant voltage lasting a predetermined sample time (e.g. 1 μs) at the input to the lead 11, then measures impedance changes in relationship to time after the generation of the voltage step. The circuit 82 measures the combined interrogating and reflected voltage waveforms while the voltage input is applied to the lead 11.

The peak current circuit 82 includes switches SW3, SW5 and SW6 for connecting, respectively, the lead 11 (through coupling capacitor C3), reference ground and the regulated voltage source $V_{DD}$ to a node A in the circuit 82. Switch SW4 connects reference ground to the pacemaker case 30. Node A is coupled via switch SW3 to the positive input to the buffer amplifier 32. Switches SW3, SW4, SW5 and SW6, tip electrode 10, lead 11, case 30, $V_{DD}$, coupling capacitor C3 and buffer amplifier 32 of the peak current circuit 82 of FIG. 7 are functionally and structurally equivalent to like-named components of FIGS. 3 and 5. In the peak current circuit 82, a step generator capacitor C4 replaces the measuring capacitor C2 of FIG. 3. In addition to the circuit elements of includes the aforementioned series resistor R8, rectifier diode D2 and peak current measuring capacitor C8.

The peak current circuit 82 employs the tip electrode 10 and lead 11 both for applying a voltage step to the patient's body, and for measuring voltage reflections returning via lead 11 that result from the applied voltage step. The controller closes switch SW6 to charge the step generator capacitor C4 to the regulated voltage source $V_{DD}$. Subsequently, the controller opens switch SW6 and closes switches SW3 and SW4 while switch SW5 is held open, thereby connecting the step generator capacitor C4 to lead 11 through a coupling capacitor C3. While the switches SW3 and SW4 are closed, step generator capacitor C4 discharges through capacitor C3 into the lead 11, thereby applying the voltage that is across step generator capacitor C4 to the lead 11. As the step voltage is applied to the lead 11, the current in peak current circuit 82 flows through the series resistor R8, establishing a voltage across the resistor. The rectifier diode D2 passes this voltage to the peak current measuring capacitor C8, so that a voltage proportional to the maximum current flowing through the resistor R8 is placed across measuring capacitor C8. In this manner, the peak current circuit 82 establishes a voltage which represents the summation of the current flowing due to the applied interrogating voltage step impulse and the current arising from impedance variations from the lead 11 and patient's body. The peak current measuring capacitor CS stores this voltage and buffer amplifier 32 later (when switch SW2 closes) transfers this voltage to the filter 23 in the manner discussed earlier in connection with the constant voltage circuit 80 of FIG. 5.

Figure 8A:
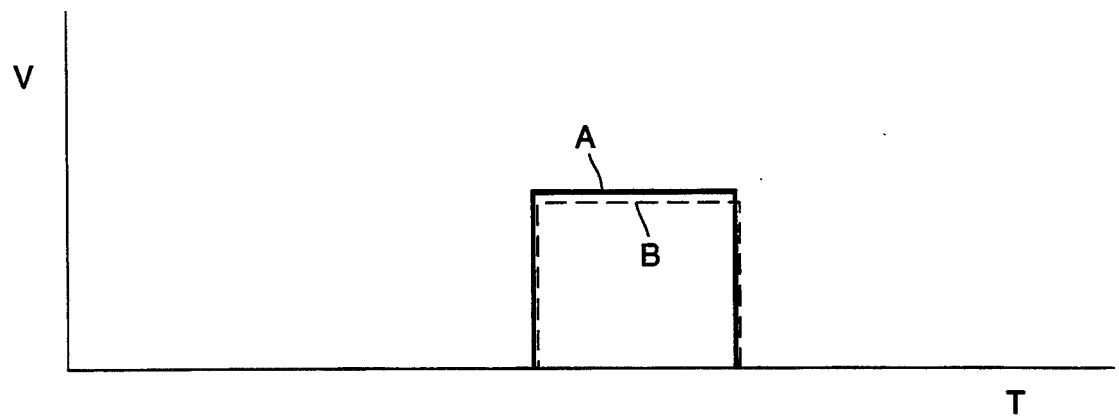
FIGS. 8A and 8B are graphical depictions of time waveforms, FIG. 8A illustrating a voltage step input applied to a lead and a measured response signal output elicited by the input, and FIG. 8B illustrating in time expanded form the current flowing as a result of the applied voltage, measured by the peak current circuit of FIG. 7.
Figure 8B:
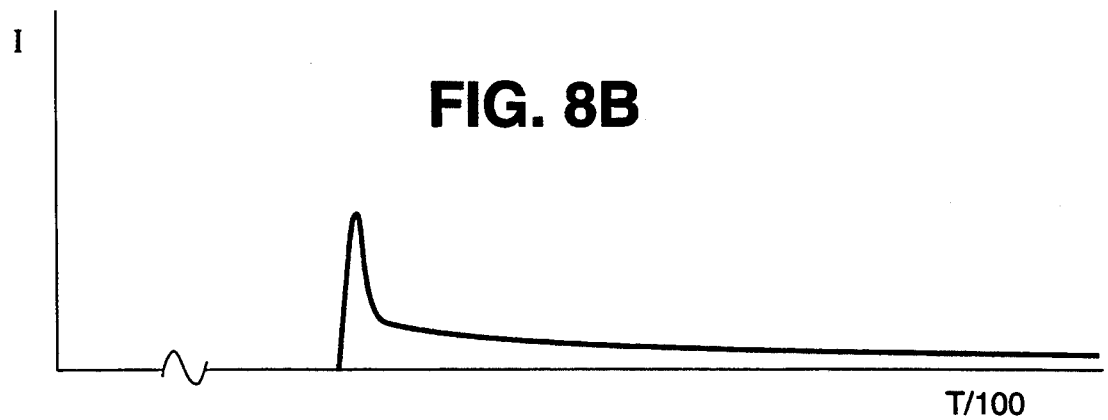

The purpose of the FIG. 7 (peak current circuit 82) embodiment of the TDR impedance sensor 14 is to restrict the time of taking the impedance measurement to a predetermined portion of the measurement field, in particular, the portion of the field proximal to the tip of the lead 11, thereby to eliminate the need for high speed switches. As indicated earlier the maximum signal amplitude reflects impedance characteristics lying beyond the distal end of the lead 11. The peak current circuit 82 is provided to facilitate the taking of impedance measurements proximal to the tip of the lead 11. For the application of a cardiac pacemaker 5 with the lead tip electrode 10 implanted in a patient's heart, impedance signals arising proximal to the distal end of the lead are a function of respiration. FIG. 8A is a graphical depiction of an applied step voltage A and a voltage response B, as measured by the peak current circuit 82. FIG. 8B illustrates the current flowing in the series resistor R8 as the voltage step is applied. For each waveform, the peak current circuit 82 determines only one value, the maximum voltage signal, which arises proximal to the end of the lead 11.

Figure 9:
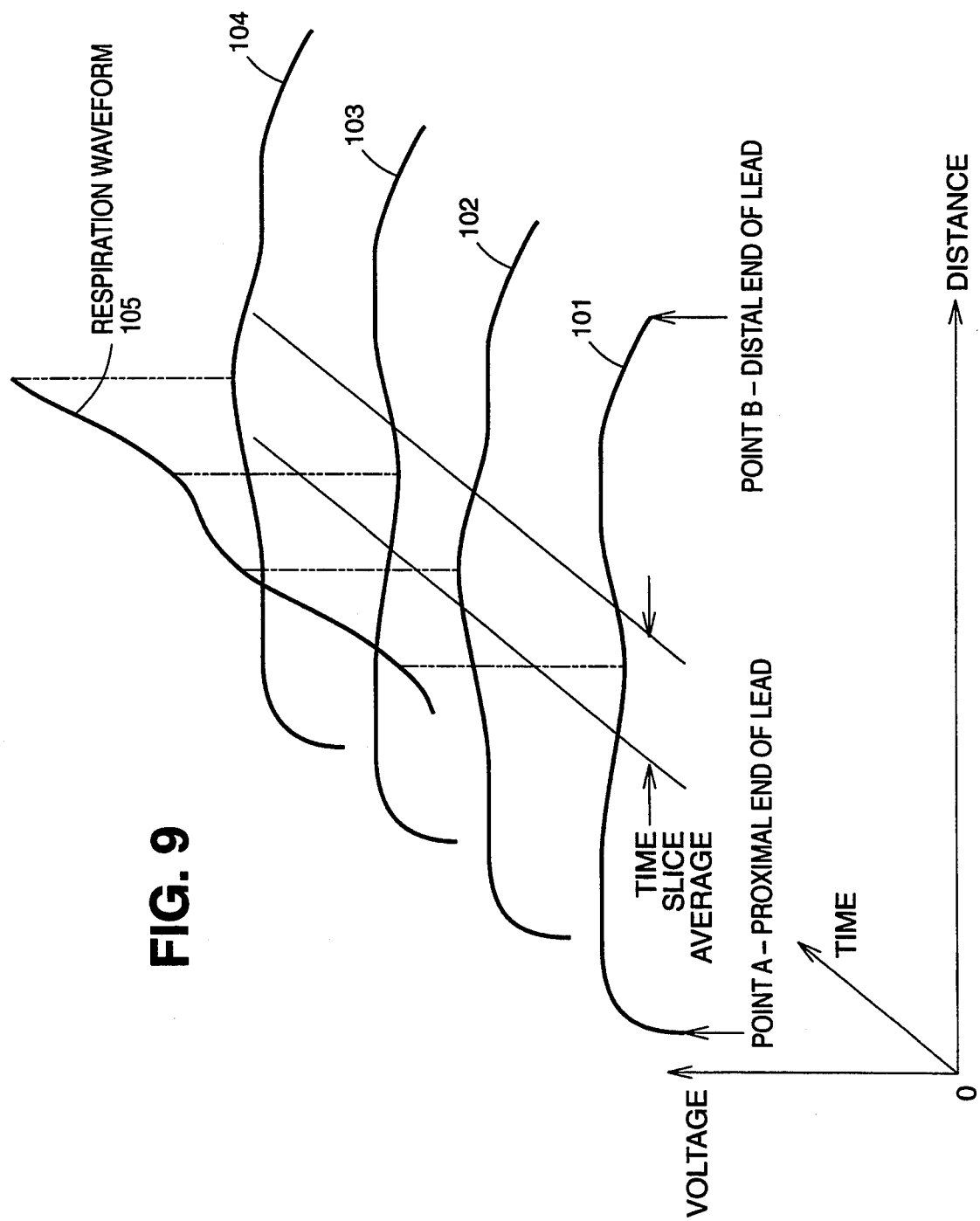
FIG. 9 illustrates selected, simulated, three-dimensional TDR waveforms.

FIG. 9 is graphical depiction of selected, simulated three-dimensional TDR waveforms. Along a horizontal distance axis, reflected voltage amplitudes change in the vertical direction in response to interrogation by an applied voltage step stimulus. Note that changes in distance along the axis correspond to changes in time since distance relates to the time-of-flight for reflections to reach the sensor following a step voltage input to the lead 11. At distance zero, point A at the proximal end of the lead at the base of the graph of FIG. 9, a voltage step is applied to lead 11 and the sensor circuit 14 measures the voltages of a first TDR waveform 101 considered in this figure. The first TDR waveform, extending generally horizontally on the three dimensional graph, illustrates the manner in which reflected voltages vary in distance down the lead 11 to its distal end (point B). The measured voltage varies as impedance variations along the lead 11 are encountered by the interrogating pulse. From point A to point B on the graph of FIG. 9, a distance and time TDR waveform resulting from a single interrogating pulse is illustrated, which extends for the lead's length. After the first waveform is measured, a second (not shown) and additional waveforms are acquired by generating voltage steps periodically after the first. For simplicity, only four TDR waveforms 101, 102, 103 and 104 are shown in FIG. 9 along the time axis, in which time relates to the time at which an interrogation voltage pulse is applied to the lead 11. These waveforms correspond to the peaks and valleys of a physiological "respiration" waveform 105, it being understood that numerous other TDR waveforms are generated in addition to those shown at 101–104 to more accurately define the respiration waveform 105 (see, e.g., FIG. 10). The voltages during a segment of each TDR waveform, called a time slice, may be measured and averaged over the length of the segment to provide a time slice average. The time slice average may be plotted in time to provide a waveform (e.g., waveform 105) indicative of a particular parameter, which may be a parameter having physiological importance such as respiration, as is depicted in the graph of FIG. 9. The position of the time slice along the distance axis determines the physiological significance of the parameter. For example, in some locations the impedance may be most influenced by body motion arising from patient respiration. At other locations, heart motion may give rise to the largest signals.

Similarly, FIG. 10 is graphical depiction of simulated TDR waveforms shown in three dimensions. Along one horizontal time axis, reflected voltage amplitudes change in the vertical direction in response to interrogation by an applied voltage step stimulus. At time zero on the bottom of the graph of FIG. 10, a voltage step is applied to a lead 11 and the sensor circuit 14 measures the voltages of a first waveform 106. The first waveform, on the right side of the three dimensional graph, illustrates the manner in which reflected voltages vary in time and, since the measuring circuit measures time-of-flight of the simulating voltage, in distance along the lead 11 (between points A and B), and beyond. The measured voltage varies as impedance variations along the lead 11 are encountered by the interrogating pulse. A discontinuity in the waveform occurs at the position (point B) of the tip electrode 10 due to the presence of a large capacitance at the tip electrode, which causes a large DC impedance change. As is shown to the right of the tip electrode 10 on the graph of FIG. 10, at locations more distal to the tip electrode 10 the interrogating voltage step continues to proceed into the patient's heart chambers and blood vessels, where additional impedance variations are reflected back to the lead 11. From time zero (the time of stimulus delivery at point A) to the rightmost position on the graph of FIG. 10, the TDR waveform 106 resulting from a single interrogating pulse extends for approximately 200 to 400 nanoseconds. After the first time waveform 106 is measured, multiple additional waveforms (e.g., 107–108 and 101–104) are acquired by generating a voltage step every 5 ms after the first, for example, to provide a sampling frequency of 200 Hz. Sampling frequencies may be widely variable depending on the type of impedance information sought by the sensor 14. Additional TDR waveforms are shown on the waveform axis extending from the bottom center to the back left side of the three dimensional graph. The waveform axis extends from the first TDR waveform 106 to a final TDR waveform 109 and relates to the time at which the interrogating voltage step is applied to the lead 11 to produce each waveform. The TDR waveforms vary in amplitude as a function of physiological parameters, as was discussed previously with regard to FIG. 9. These variations are depicted as fluctuations in the three dimensional signal shown in FIG. 10. Here, variations from the proximal end of the lead 11 (at time 0) to the tip electrode 10 indicate impedance fluctuations caused by patient respiration. Variations occurring beyond the tip electrode 10 (e.g., beyond point B) relate to impedance changes arising from heart motion. For a particular individual and implantation, these signals may be widely variable. Placement of the lead and other factors influence the amplitude and shape of the impedance changes. A physiological "cardiac" waveform that may be generated from the impedance variations due to heart motion is shown at In one example of a data acquisition, the sensor 14 acquires multiple 100 point TDR waveforms, such as waveforms 101–104 and 106–109, triggered by the voltage pulse generator 18, until a total of 200 such TDR waveforms are acquired and stored. Each of such waveforms is defined by 100 data point samples, spaced at the sample rate of one sample per 1 nanosecond.

Referring now to FIG. 11A, a simulated graph of a TDR voltage waveform is shown. This TDR waveform may be considered one of the several waveforms shown in FIGS. 9 and 10, for example waveform 101. The TDR waveform signal may be integrated or averaged over a time window, such as respiration time slice window 115 as shown. For example, the TDR sensor circuit 4 of FIG. 3 may open and close the switches SW2, SW3, SW4 and SW5 to define the illustrated window. Furthermore, the digitizing oscilloscope 66 of the TDR impedance sensor 60 of FIG. 4A may sample multiple points within the designated window and the computer system 70 may average these samples. Additionally, the peak current circuit 82 of FIG. 7 may measure the voltage corresponding to the peak current which flows during the designated window.

Referring now to FIG. 11B, a respiration waveform 105 may be derived from voltage measurements in the selected window depicted in FIG. 11A of many sequential TDR voltage waveforms such as 101, 106–108 . . . n. These values may be plotted, stored for analysis, or processed to derive physiologically-valuable data. For example, the respiration waveform 105 may be processed to derive a pacing rate for a rate-adaptive pacemaker 5.

Figure 12A:
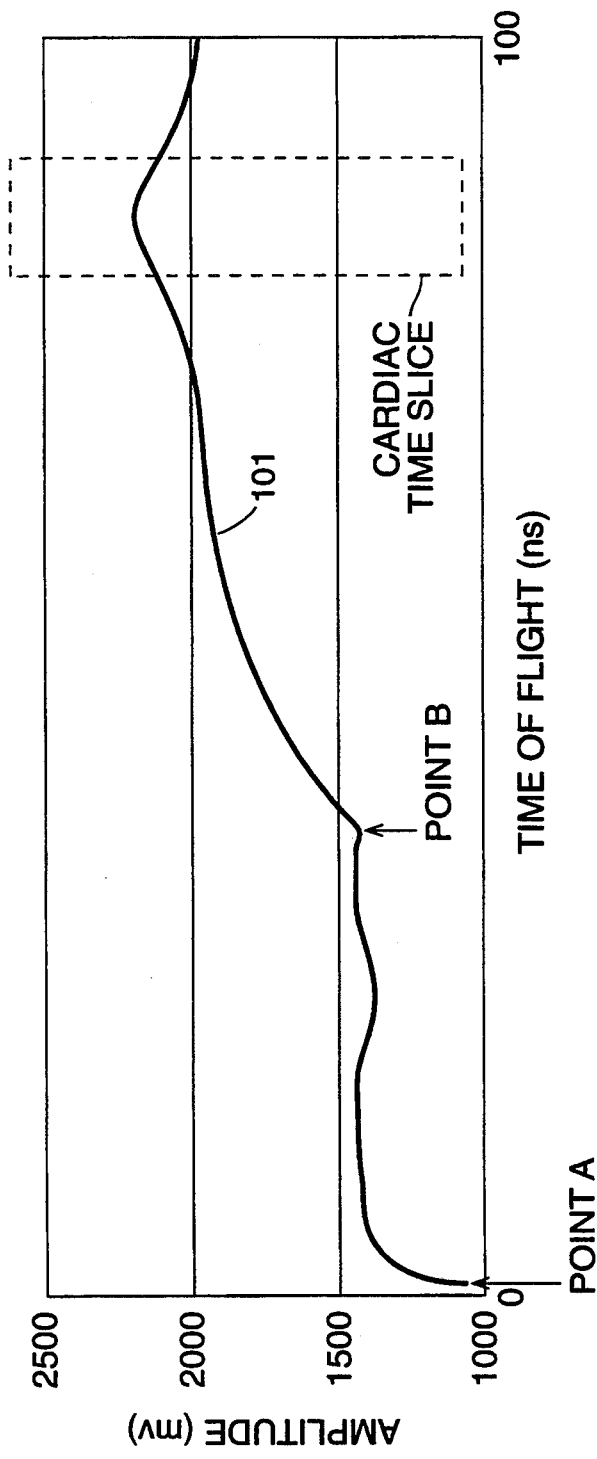
FIGS. 12A and 12B depict, respectively, simulated graphs of a TDR voltage waveform and a cardiac motion waveform derived from voltage measurements made during corresponding selected windows of many sequential TDR voltage waveforms.

Referring now to FIG. 12A, a simulated graph of a TDR voltage waveform is shown. This TDR waveform may also be considered one of the several waveforms shown in FIGS. 9 and 10, for example waveform 101, and integrated or averaged over a time window, such as cardiac time slice window 120, as shown. For example, the TDR sensor circuit 14 of FIG. 3 may open and close the switches SW2, SW3, SW4 and SW5 to define the illustrated window or the digitizing oscilloscope 66 of the TDR impedance sensor 60 of FIG. 4A may sample multiple points within the designated window and the computer system 70 may average these samples. Furthermore, the constant voltage circuit 80 of FIG. 5 may measure the voltage corresponding to the voltage during the designated window.

Figure 12B:
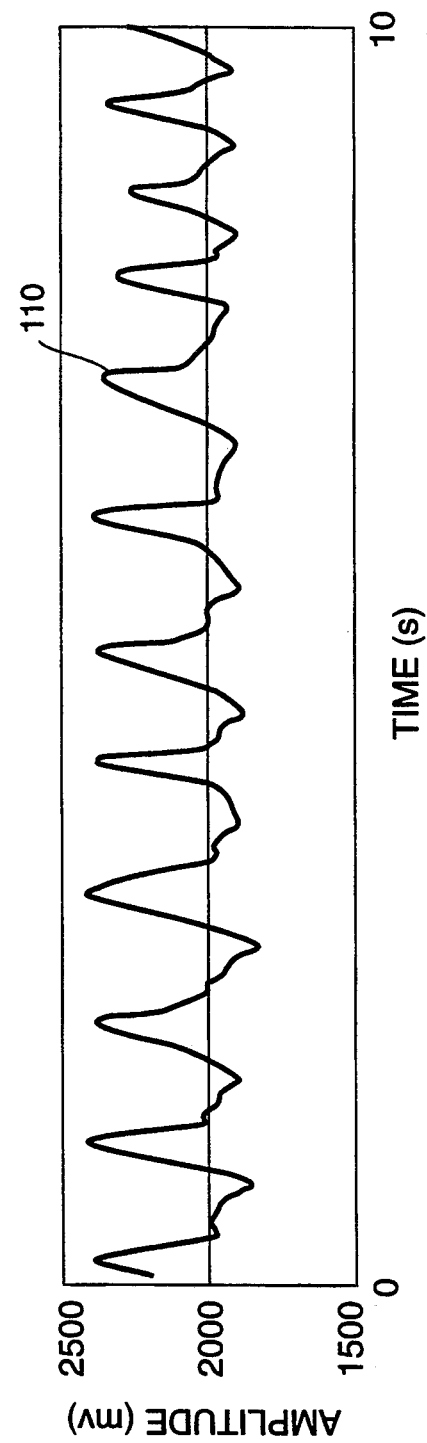

Referring now to FIG. 12B, a cardiac motion waveform 110 may be derived from voltage measurements in the selected window depicted in FIG. 12A of many sequential TDR voltage waveforms such as 101, 106–108 . . . n. These values may be plotted, stored for analysis, or processed to derive physiological data.

From the foregoing discussion, it is apparent that the present invention provides a time domain reflectometry impedance sensor that fundamentally differs from previous methods of measuring internal body impedance. This impedance measurement method is valuable for reducing the problem of the electrode-electrolyte polarization effects. The invention accomplishes substantial improvements in distinguishing impedance signals arising from diverse physiological origins such as respiration and heart motion, and improving physiological signal fidelity by reducing signals arising from the electrode-electrolyte interface. Additionally, the present invention provides a method and apparatus for testing implanted pacing leads for breakage and imperfections.

While particular embodiments of this invention have been shown and described, it will be obvious to those skilled in the art that various other changes and modifications may be made without departing from this invention in its broader aspects, and it is, therefore, aimed in the appended claims to cover all such changes and modifications as fall within the true spirit and scope of this invention.

We claim:

1. A sensor in a medical device for measuring a patient's internal body impedance, comprising:
   a transmission line adapted to be implanted in the patient's body tissue;
   means for applying an electrical stimulation to said transmission line to propagate the electrical stimulation through the patient's tissue;
   means for measuring a reflected electrical signal in said transmission line that results from reflections of the propagated electrical stimulation due to impedance variations in the patient's tissue, said impedance variations corresponding to a physiological function; and
   means for deriving an impedance signal as a function of the reflected electrical signal to detect said physiological function.

2. A sensor in accordance with claim 1, wherein said transmission line comprises a lead having a distal electrode therein.

3. A sensor in accordance with claim 1, wherein said transmission line comprises a coiled conductor.

4. A sensor in accordance with any one of claims 1, 2 or 3, wherein said applying means generates an electrical stimulation in the form of a stimulus selected from a group including a step voltage, a step current, a pulse voltage and a pulse current.

5. A sensor in a medical device for measuring a patient's time-varying internal body impedance, comprising:
   a transmission line adapted to be implanted in the patient's body tissue;
   means for applying an electrical stimulation to said transmission line to propagate the electrical stimulation through the patient's tissue;
   means for measuring a time-varying reflected electrical signal in said transmission line that results from reflections of the propagated electrical stimulation due to impedance variations in the patient's tissue, said impedance variations corresponding to a physiological function;
   means for distinguishing electrical signals arising within at least one predetermined time interval of the time-varying reflected electrical signal from electrical signals arising outside of such interval; and
   means for deriving an impedance signal as a function of the distinguished electrical signals to detect a parameter of said physiological function.

6. A sensor in accordance with claim 5, wherein said transmission line is selected from a group including a lead having a distal electrode therein, and a coiled conductor.

7. A sensor in accordance with claim 5, wherein said distinguishing means further comprises a timer responsive to the application of the applied electrical stimulus for timing a predetermined delay interval and a corresponding predetermined sample duration interval for such application, said corresponding sample duration interval being timed to occur subsequent to said delay interval, wherein said measuring means is responsive to termination of the predetermined delay interval and is operational during said corresponding sample duration interval for measuring said time-varying reflected electrical signal, said delay interval and said sample duration interval being predetermined to select a range of distance from said transmission line for such measurement, and wherein said deriving means includes a controller which derives a range-selected impedance signal as a function of the electrical signal distinguished in said at least one predetermined time interval.

8. A sensor in accordance with claim 7, wherein said controller further comprises:
   means for repetitively triggering said applying means while maintaining said predetermined delay interval and said predetermined sample duration interval constant; and
   means for collecting said range-selected impedance signals resulting from said repetitive triggering into a time varying range-selected impedance signal.

9. A sensor in accordance with anyone of claims 5-8, wherein said parameter is derived as a function of a range-selected impedance signal, said parameter being in the form of a signal selected from a group consisting of a respiration signal and a heart motion signal.

10. A sensor in accordance with any one of claims 5-8, wherein said applying means generates an electrical stimulation in the form of a stimulus selected from a group including a step voltage, a step current, a pulse voltage and a pulse current.

11. A sensor in accordance with any one of claims 5-8, wherein said distinguishing means utilizes a constant voltage circuit in distinguishing electrical signals arising within said at least one predetermined time interval from those arising outside of such interval.

12. A sensor in accordance with claim 11, wherein said parameter is in the form of a signal selected from a group including a respiration signal and a heart motion signal.

13. A sensor in accordance with claim 11, wherein said applying means generates an electrical stimulation in the form of a stimulus selected from a group including a step voltage, a step current, a pulse voltage and a pulse current.

14. A sensor in a medical device for measuring a patient's internal body impedance, comprising:
   a lead adapted to be implanted in the patient's cardiovascular system;
   means for applying a voltage pulse to said lead, the voltage pulse being substantially in the form of a step function;
   means for measuring a reflection voltage waveform in said lead that results from reflections of the applied voltage pulse due to impedance variations of the patient's tissues, said impedance variations corresponding to a physiological parameter, said reflections being received in said lead; and
   means for deriving an impedance signal as a function of the reflection voltage waveform to detect said physiological parameter.

15. A sensor in accordance with claim 14, wherein said applying means generates a voltage pulse having a pulse width in the range from 1 ns to 1 ms.

16. A sensor in a medical device for measuring a patient's internal body impedance, comprising:
   a lead adapted to be implanted in the patient's blood vessels and heart chambers, said lead extending from a proximal end to a distal end;
   means coupled to said lead at its proximal end for applying a voltage pulse to said lead;
   means for measuring a reflection voltage waveform from said lead that results from reflections of the applied voltage pulse due to impedance variations, said reflections being received in said lead from its proximal end to its distal end and due to impedance variations arising distally beyond said lead along said patient blood vessels and heart chambers, said impedance variations arising in said patient's blood vessels and heart chambers due to a physiological parameter; and means for deriving an impedance signal as a function of the reflection voltage waveform to determine said physiological parameter.

17. A sensor in a medical device for measuring a patient's internal body impedance, comprising:

a lead adapted to be implanted in the patient's blood vessels and heart chambers, said lead extending from a proximal end to a distal end;

a pulse generator coupled to said lead at its proximal end for applying a voltage pulse to said lead;

a timer responsive to the application of the voltage pulse by said pulse generator for timing a predetermined delay interval and a predetermined sample duration interval, said sample duration interval being timed to occur subsequent to said delay interval;

a measurement circuit activated in response to termination of the predetermined delay interval and operational until termination of said sample duration interval for measuring a reflection voltage waveform on said implanted lead that results from reflections of the applied voltage pulse due to impedance variations of the patient's tissues corresponding to a physiological parameter, said reflections being received in said lead from its proximal end to its distal end and arising distally beyond said lead in blood vessels and heart chambers of said patient, said delay interval and said sample duration interval being predetermined to select a range of distance from the proximal end of said lead for such measurement; and a controller for deriving a range-selected impedance signal as a function of said reflection voltage waveform to detect said parameter.

18. A sensor in accordance with claim 17, wherein said controller further comprises:

means for repetitively triggering said pulse generator while maintaining said predetermined delay interval and said predetermined sample duration interval constant; and means for collecting said range-selected impedance signals resulting from said repetitive triggering into a time-varying range-selected impedance signal.

19. A sensor in accordance with claim 18, wherein said pulse generator applies a voltage pulse in the form of a step function having an amplitude in the range off from 1 $\mu$V to 100 $\mu$V and a pulse width in the range from 1 ns to 5 ms.

20. A sensor in accordance with claim 19, wherein said predetermined delay intervals occur within a range of from 1 ns to 200 ns and said predetermined sample duration interval 21. A sensor in accordance with claim 20, wherein said triggering means triggers said pulse generator at a rate in the range from 0.1 Hz to 500 Hz.

22. A sensor in a medical device for measuring a patient's internal body impedance, comprising:

a lead adapted to be implanted in the patient's cardiovascular system;

a pulse generator for applying a voltage pulse to said lead, the voltage pulse being substantially in the form of a step function;

a detector for measuring a reflection voltage waveform in said lead that results from reflections of the applied voltage pulse due to impedance variations along said lead corresponding to a physiological parameter; and a controller adapted to derive an impedance signal as a function of the reflection voltage waveform for the detection of said parameter.

23. A sensor in a medical device for measuring a patient's internal body impedance, comprising:

a lead adapted to be implanted in the patient's cardiovascular system;

a time domain reflectometer (TDR) coupled to said lead, said TDR being configured to transmit a series of signal pulses through said lead and to monitor signals that arise due to reflections of the applied voltage pulse from impedance variations of the patient's tissues corresponding to a physiological parameter; and a controller coupled to said TDR, said controller being adapted to sample said monitored signals and to define an impedance signal of interest from said sampled signals.

24. A method of measuring internal body impedance along a lead implanted in a patient's cardiovascular system, comprising the steps of:

applying a step voltage pulse to the lead, the voltage pulse being substantially in the form of a step function;

measuring a reflection voltage waveform in the lead that results from reflections of the applied voltage pulse due to impedance variations of the patient's tissues corresponding to a physiological parameter; and deriving an impedance signal as a function of the reflection voltage waveform.

25. A method of measuring internal body impedance along and distal to a lead implanted in a patient's cardiovascular system, comprising the steps of:

applying a voltage signal to the lead;

measuring a reflection voltage waveform in the lead that results from reflections of the applied voltage pulse due to impedance variations of the patient's tissues corresponding to a physiological parameter; and deriving an impedance signal as a function of the reflection voltage waveform.

26. A method of measuring internal body impedance along and distal to a lead implanted in a patient's cardiovascular system, comprising the steps of:

predetermining a longitudinal region of interest along and distal to the implanted lead from a proximal region boundary to a distal region boundary;

deriving a delay interval corresponding to the time required for a voltage pulse to traverse and return from the proximal region boundary;

deriving a sample duration interval corresponding to the time required for a voltage pulse to traverse and return from the distal region boundary, less the time of the delay interval;

applying a voltage signal to the implanted lead;

timing the derived delay interval following said applying step and timing the derived sample duration interval following the timeout of the delay interval;

measuring a reflection voltage waveform in the implanted lead during the sample duration interval, the reflection voltage waveform resulting from reflections of the applied voltage pulse due to impedance variations of the patient's tissues corresponding to a physiological parameter, said reflections being received along the lead from its proximal end to its distal end and arising distally beyond the lead in blood vessels and heart chambers of the patient; and deriving a range-selected impedance signal as a function of the reflection voltage waveform to detect said parameter.

27. A method according to any one of claims 24–26, wherein said applying step includes the sub-step of repetitively applying said voltage pulse to said lead, and wherein said deriving step includes the sub-step of collecting said impedance signals resulting from said repetitive voltage pulse applications into a time-varing impedance signal.

28. A patient-implantable heart pacemaker adapted for measuring at least one physiological parameter, comprising:

a lead adapted to be implanted in the patient's blood vessels and heart chambers, said lead extending from a proximal end to a distal end;

means for applying an electrical stimulation to said lead to propagate the electrical stimulation through the patient's tissue;

means for measuring a time-varying reflected electrical signal from said implanted lead that results from reflections of the propagated electrical stimulation, the reflections arising due to impedance variations in the patient's tissue and corresponding to a physiological parameter;

means for distinguishing at least one predetermined time interval of the time-varying reflected electrical signal from other potential time intervals thereof; and means for deriving an impedance signal as a function of the distinguished at least one predetermined time interval of the time-varying reflected electrical signal to detect said parameter.

29. A pacemaker in accordance with claim 28, wherein said distinguishing means further comprises a timer responsive to the application of the applied electrical stimulus for timing a predetermined delay interval and a corresponding predetermined sample duration interval for such application, said corresponding sample duration interval being timed to occur subsequent to said delay interval, wherein said measuring means is responsive to termination of the predetermined delay interval and is operational during said corresponding sample duration interval for measuring said time-varying reflected electrical signal, said delay interval and said sample duration interval being predetermined to select a range of distance from said lead for such measurement, and wherein said deriving means includes a controller for deriving a range-selected impedance signal as a function of the reflected electrical signal distinguished in said at least one predetermined time interval.

30. A pacemaker in accordance with claim 26, wherein said physiological parameter is derived as a function of said range-selected impedance signal, said parameter being in the form of a signal selected from a group including a respiration signal and a heart motion signal.

31. A pacemaker in accordance with claim 29, wherein said applying means is adapted to generate an electrical stimulation in the form of a stimulus selected from a group including a step voltage, a step current, a pulse voltage and a pulse current.

32. A pacemaker in accordance with claim 28, wherein said distinguishing means utilizes a constant voltage circuit in distinguishing said at least one predetermined time interval of the time-varying reflected electrical signal from other potential time intervals thereof.

33. A pacemaker in accordance with claim 32, wherein said parameter is in the form of a signal selected from a group including a respiration signal and a heart motion signal.

34. A pacemaker in accordance with claim 32, wherein said applying means generates an electrical stimulation in the form of a stimulus selected from a group including a step voltage and a pulse voltage.

* * * * *